(12) United States Patent
Bentley et al.

(10) Patent No.: US 6,610,685 B2
(45) Date of Patent: Aug. 26, 2003

(54) FUSED INDOLE DERIVATIVES

(75) Inventors: Jonathan Mark Bentley, Wokingham (GB); Michael John Bickerdike, Wokingham (GB); Paul Hebeisen, Basie (CH); Guy Anthony Kennett, Wokingham (GB); Sean Lightowler, Wokingham (GB); Patrizio Mattei, Riehen (CH); Jacques Mizrahi, Basle (CH); Timothy James Morley, Wokingham (GB); Jean-Marc Plancher, Knoeringue (FR); Hans Richter, Grenzach-Wyhlen (DE); Stephan Roever, Inzlingen (DE); Sven Taylor, Riedisheim (FR); Steven Paul Vickers, Wokingham (GB)

(73) Assignees: Hoffmann-La Roche Inc., Nutley, NJ (US); Vernalis Research Limited, Workingham (GB)

( * ) Notice: Subject to any disclaimer, the term of this patent is extended or adjusted under 35 U.S.C. 154(b) by 0 days.

(21) Appl. No.: 10/017,978

(22) Filed: Dec. 14, 2001

(65) Prior Publication Data

US 2002/0160997 A1 Oct. 31, 2002

(30) Foreign Application Priority Data

Dec. 27, 2000 (GB) .............................. 0031724
Aug. 14, 2001 (GB) .............................. 0119820

(51) Int. Cl.$^7$ ........................ C07D 487/04; A61K 31/40
(52) U.S. Cl. .................. 514/214.01; 514/294; 514/411; 540/586; 546/94; 548/428
(58) Field of Search .................... 548/428; 546/94; 540/586; 514/411, 294, 214.01

(56) References Cited

U.S. PATENT DOCUMENTS

| | | | |
|---|---|---|---|
| 4,598,089 A | 7/1986 | Hadvary et al. ............. | 514/449 |
| 6,004,996 A | 12/1999 | Shah et al. .................. | 514/449 |

FOREIGN PATENT DOCUMENTS

| | | |
|---|---|---|
| EP | 185 359 | 6/1986 |
| EP | 189 577 | 8/1986 |
| EP | 443 449 | 8/1991 |
| EP | 524 495 | 1/1993 |
| EP | 655 440 | 5/1995 |
| EP | 0 657 426 | 6/1995 |
| EP | 1 132 389 | 12/2001 |
| WO | WO 98/30548 | 7/1998 |
| WO | WO 99/34786 | 7/1999 |
| WO | WO 00/09122 | 2/2000 |
| WO | WO 00/09123 | 2/2000 |
| WO | WO 00/12510 | 3/2000 |
| WO | WO 00/35922 | 6/2000 |

OTHER PUBLICATIONS

Kiuchi et al., PubMed Abstract (Nippon Rinsho 52(5): 1190–5), May 1994.*
Damasio, Alzheimer's Disease and Related Dementias, Cecil Textbook of Medicine, 20th Edition, vol. 2, pp. 1992–1996, 1996.*
Layzer, Degenerative Diseases of the Nervous System, Cecil Textbook of Medicine, 20th Edition, vol. 2, pp. 2050–2057, 1996.*
Parker, "Obesity: Trends and Treatments", Scrip Reports, PJB Publications Limited, (1996).
Kennett et al., Psychopharmacology, 96, pp. 93–100 (1988).
Kennett et al., Eur. J. Pharmacol., 141, pp. 429–435 (1987).
Kitchener et al., Psychopharmacology, 113, pp. 369–377 (1994).
Walsh et al., Psychopharmacology, 116, pp. 120–122 (1994).
Sargeant et al., Psychopharmacology, 133, pp. 309–312 (1997).
Tecott et al., Nature, vol. 374, pp. 542–546 (1995).
Kennett et al., Neuropharmacology, vol. 36, pp. 609–620 (1997).
Hoyer et al., European J. Pharmacology, 118, pp. 13–23 (1985).
Schmuck et al., FEBS Letters, 342, pp. 85–90 (1994).
McKenna et al., J. Neuroscience, 9, pp. 3482–3490 (1989).
MacDougald et al., Current Biology, vol. 5, pp. 618–621 (1995).
Keller et al., Trends Endocrin. Metab., 4, pp. 291–296 (1993).
Cheng et al., Biochem. Pharmacol., 22(23) pp. 3099–3108 (1973).
Kondo et al., J. Org. Chem., 62, pp. 6507–6511 (1997).
Mutoh et al., J. Antibiot., 47(12), pp. 1369–1375 (1994).
Abstract CA 2132887, 1995.
Abstract CA 2153937, 1996.

* cited by examiner

*Primary Examiner*—Deepak Rao
(74) *Attorney, Agent, or Firm*—George W. Johnston; Dennis P. Tramaloni; Lyman H. Smith

(57) ABSTRACT

The present invention is a chemical compound of formula (I)

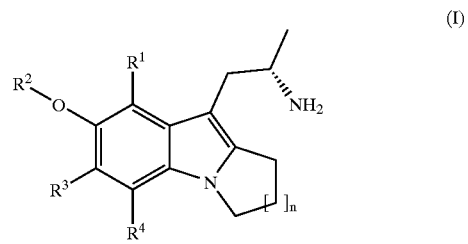

(I)

or a pharmaceutically acceptable salt, solvate and ester thereof, wherein $R^1$ to $R^4$ and n are as defined in the specification. A compound of formula 1 is useful as a pharmaceutical composition for the treatment or prevention of disorders of the central nervous system, cardiovascular disorders, gastrointestinal disorders, diabetes, obesity and sleep apnoea.

47 Claims, No Drawings

FUSED INDOLE DERIVATIVES

BACKGROUND

It has been recognised that obesity is a disease process influenced by environmental factors in which the traditional weight loss methods of dieting and exercise need to be supplemented by therapeutic products (S. Parker, "Obesity: Trends and Treatments", Scrip Reports, PJB Publications Ltd, 1996).

Whether someone is classified as overweight or obese is generally determined on the basis of their body mass index (BMI) which is calculated by dividing body weight (kg) by height squared (m$^2$). Thus, the units of BMI are kg/m$^2$ and it is possible to calculate the BMI range associated with minimum mortality in each decade of life. Overweight is defined as a BMI in the range 25–30 kg/m$^2$. Obesity is a BMI greater than 30 kg/m$^2$. There are problems with this definition in that it does not take into account the proportion of body mass that is muscle in relation to fat (adipose tissue). To account for this, obesity can also be defined on the basis of body fat content: greater than 25% and 30% in males and females, respectively.

As the BMI increases there is an increased risk of death from a variety of causes that is independent of other risk factors. The most common diseases associated with obesity are cardiovascular disease (particularly hypertension), diabetes (obesity aggravates the development of diabetes), gall bladder disease (particularly cancer) and reproductive diseases. Research has shown that even a modest reduction in body weight can correspond to a significant reduction in the risk of developing coronary heart disease.

Compounds marketed as anti-obesity agents include Orlistat (XENICAL®) and Sibutramine. Orlistat (a lipase inhibitor) inhibits fat absorption directly and tends to produce a high incidence of unpleasant (though relatively harmless) side-effects such as diarrhoea. Sibutramine (a mixed 5-HT/noradrenaline reuptake inhibitor) can increase blood pressure and heart rate in some patients. The serotonin releaser/reuptake inhibitors fenfluramine (Pondimin®) and dexfenfluramine (Redux™) have been reported to decrease food intake and body weight over a prolonged period (greater than 6 months). However, both products were withdrawn after reports of preliminary evidence of heart valve abnormalities associated with their use. There is therefore a need for the development of a safer anti-obesity agent.

The non-selective 5-HT$_{2C}$ receptor agonists/partial agonists m-chlorophenylpiperazine (mCPP) and trifluoromethylphenylpiperazine (TFMPP) have been shown to reduce food intake in rats (G. A. Kennett and G. Curzon, Psychopharmacol., 1988, 96, 93–100; G. A. Kennett, C. T. Dourish and G. Curzon, Eur. J. Pharmacol., 1987, 141, 429–435) and to accelerate the appearance of the behavioural satiety sequence (S. J. Kitchener and C. T. Dourish, Psychopharmacol., 1994, 113, 369–377). Recent findings from studies with mCPP in normal human volunteers and obese subjects have also shown decreases in food intake. Thus, a single dose of mCPP decreased food intake in female volunteers (A. E. S. Walsh et al., Psychopharmacol., 1994, 116, 120–122) and decreased the appetite and body weight of obese male and female subjects during subchronic treatment for a 14 day period (P. A. Sargeant et al., Psychopharmacol., 1997, 133, 309–312). The anorectic action of mCPP is absent in 5-HT$_{2C}$ receptor knockout mutant mice (L. H. Tecott et al., Nature, 1995, 374, 542–546) and is antagonised by the 5-HT$_{2C}$ receptor antagonist SB-242084 in rats (G. A. Kennett et al., Neuropharmacol., 1997, 36, 609–620). It seems therefore that mCPP decreases food intake via an agonist action at the 5-HT$_{2C}$ receptor.

Other compounds which have been proposed as 5-HT$_{2C}$ receptor agonists for use in the treatment of obesity include the substituted 1-aminoethyl indoles disclosed in EP-A-0655440. CA-2132887 and CA-2153937 disclose that tricyclic 1-aminoethylpyrrole derivatives and tricyclic 1-aminoethyl pyrazole derivatives bind to 5-HT$_{2C}$ receptors and may be used in the treatment of obesity. WO-A-98/30548 discloses aminoalkylindazole compounds as 5-HT$_{2C}$ agonists for the treatment of CNS diseases and appetite regulation disorders. WO 00/35922 discloses 2,3,4,4a-tetrahydro-1H-pyrazino[1,2-a]quinoxalin-5(6H)ones as 5HT$_{2C}$ agonists.

Diabetes is a disease in which a patient's ability to control glucose levels in blood is impaired, because the ability to respond properly to the action of insulin has been partially lost. In type II diabetes, often referred to as non-insulin dependent diabetes mellitus (NIDDM), which afflicts 80–90% of all diabetic patients in developed countries, the Islets of Langerhans in the pancreas still produce insulin. However, the target organs, mainly muscle, liver and adipose tissue, exhibit a profound resistance to insulin stimulation, thus the body compensates by producing abnormally high levels of insulin. In the later stages of the disease, however, insulin secretion decreases due to pancreas exhaustion.

Current first line treatment for diabetes generally involves adoption of a diet low in fat and glucose and taking regular exercise. However, compliance can be moderate and as the disease progresses, treatment with hypoglycemic drugs, e.g. sulfonylureas or metformin, becomes necessary. A promising new class of drugs has recently been introduced that resensitize patients to their own insulin (insulin sensitizers), thereby reverting blood glucose and triglyceride levels to normal, and thus abolishing, or at least reducing, the requirement for exogenous insulin. Troglitazone (Resulin™) and rosiglitazone (Avandia™) belong to the thiazolidinediones (TZD) class of PPARγ-agonists and were the first representatives of the class approved for NIDDM treatment in several countries. These compounds, however, suffer from side effects including rare but severe liver toxicity (as seen with troglitazone), and increased body weight in humans. Therefore, new, better and more efficacious drugs for the treatment of conditions involving hyperglycemia, particularly NIDDM are urgently needed. Recent studies provided evidence that coagonism of PPARα and PPARγ would result in compounds with enhanced therapeutic potential, i. e. with an improved lipid profile effect on top of the normalization of glucose- and insulin-levels (Keller and Wahli: Trends Endocrin. Metab. 1993; 4:291–296, Macdonald and Lane: Current Biology Vol.5 pp.618–621 (1995)). The novel compounds of the present invention can be used as efficacious drugs for the treatment and prevention of diabetes, particularly of non-insulin dependent diabetes mellitus.

SUMMARY

The present invention is a new indole derivative, processes and intermediates for its preparation, to pharmaceutical compositions containing the compound of the invention and to a method of treatment using the compound. The active compound of the present invention is useful in treating obesity, diabetes and other disorders.

The invention is a compound of formula I or a pharmaceutically acceptable salt, solvate or ester thereof.

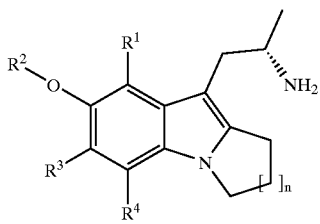

(I)

wherein
R$^1$ is hydrogen or fluoro;
R$^2$ is selected from the group consisting of methyl, ethyl, cyclopropyl, aralkyl, heteroarylalkyl, alkoxyalkyl, 3-oxetanyl, 3-tetrahydrofuranyl, 2-tetrahydrofuranylmethyl, 3-tetrahydrofuranylmethyl and hydroxyalkyl, wherein hydroxyalkyl and alkoxyalkyl are optionally independently substituted with monofluoromethyl, difluoromethyl, trifluoromethyl, alkoxy or hydroxy;
R$^3$ is hydrogen or fluoro;
R$^4$ is hydrogen or methyl; and
n is 1, 2 or 3;
or a pharmaceutically acceptable salt, solvate ester thereof, with the proviso that at least one of R$^1$ and R$^3$ is fluoro when R$^2$ is methyl.

It is an object of this invention to provide selective, directly acting 5HT$_2$ receptor ligands according to formula I for use in therapy and particularly for use as anti-obesity agents. It is a further object of this invention to provide directly acting ligands according to formula I, selective for 5-HT$_{2B}$ and/or 5-HT$_{2C}$ receptors, for use in therapy and particularly for use as anti-obesity agents. It is a further object of this invention to provide selective, directly acting 5-HT$_{2C}$ receptor ligands according to formula I, preferably 5-HT$_{2C}$ receptor agonists, for use in therapy and particularly for use as anti-obesity agents.

The compounds of formula (I) are useful in the treatment and/or prevention of disorders involving elevated plasma blood glucose, particularly diabetes mellitus (including Type II or non-insulin dependent diabetes mellitus (NIDDM); Type I or insulin dependent diabetes mellitus (IDDM); and Type III or malnutrition-related diabetes). The diabetes may be diabetes secondary to pancreatic disease; or diabetes related to steroid use. The compounds of formula (I) are also useful in the treatment and/or prevention of the sequelae of hyperglycaemia; in the treatment and/or prevention of diabetic complications; and in the treatment of insulin dependence.

The invention is of particular use in the treatment or prevention of diabetes mellitus (including Type II or non-insulin dependent diabetes mellitus (NIDDM); Type I or insulin dependent diabetes mellitus (IDDM); and Type III or malnutrition-related diabetes), and particularly in the treatment or prevention of Type II diabetes.

The present invention encompasses a method of treatment comprising administering an effective amount of a compound of formula I to a person in need of treatment of acute and/or chronic treatment and/or prevention of disorders involving elevated plasma blood glucose, particularly the acute and/or chronic treatment of disorders involving elevated plasma blood glucose, and especially acute treatment of disorders involving elevated plasma blood glucose.

DETAILED DESCRIPTION

In the present description the term "alkyl", alone or in combination, signifies a straight-chain or branched-chain alkyl group with 1 to 8 carbon atoms, preferably a straight or branched-chain alkyl group with 1–4 carbon atoms. Examples of straight-chain and branched C$_1$–C$_8$ alkyl groups are methyl, ethyl, propyl, isopropyl, butyl, isobutyl, tert.-butyl, the isomeric pentyls, the isomeric hexyls, the isomeric heptyls and the isomeric octyls, preferably methyl, ethyl, propyl and isopropyl. Particularly preferred are methyl and ethyl.

The term "cycloalkyl", alone or in combination, signifies a cycloalkyl ring with 3 to 8 carbon atoms and preferably a cycloalkyl ring with 3 to 6 carbon atoms. Examples of C$_3$–C$_8$ cycloalkyl are cyclopropyl, methyl-cyclopropyl, dimethylcyclopropyl, cyclobutyl, methyl-cyclobutyl, cyclopentyl, methyl-cyclopentyl, cyclohexyl, methylcyclohexyl, dimethyl-cyclohexyl, cycloheptyl and cyclooctyl, preferably cyclo-propyl.

The term "alkoxy", alone or in combination, signifies a group of the formula alkyl-O— in which the term "alkyl" has the previously given significance, such as methoxy, ethoxy, n-propoxy, isopropoxy, n-butoxy, isobutoxy, sec.butoxy and tert. butoxy, preferably methoxy and ethoxy.

The term "aryl" means alone or in combination a phenyl or a naphthyl group which can be substituted by one or several, preferably one to three substituents chosen from alkyl, cycloalkyl, alkoxy, halogen, carboxy, hydroxy, amino, nitro, trifluoromethyl, cyano and the like. Examples of aryl are phenyl, p-tolyl, methoxyphenyl, tert. butoxyphenyl, fluorophenyl, chlorophenyl, hydroxyphenyl, naphthyl, 4-cyanophenyl and 3-cyanophenyl.

The term "heteroaryl", alone or in combination, signifies an aromatic 5- or 6-membered ring comprising 1 to 3 atoms independently selected from nitrogen, oxygen or sulfur. Optionally, the heteroaryl ring can be substituted on one or more carbon atoms with halogen, alkyl, alkoxy and cyano. Examples of heteroaryl rings include furyl, pyridyl, 1,2-, 1,3- and 1,4-diazinyl, thienyl, isoxazolyl, oxazolyl, thiazolyl and pyrrolyl.

The term "aralkyl", alone or in combination, signifies an alkyl group as previously defined in which one or several, preferably one hydrogen atom has been replaced by an aryl group as previously defined. An example is benzyl.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substituents together forming a ring, such as, for example, —NH$_2$, methylamino, ethylamino, dimethylamino, diethylamino, methylethylamino, pyrrolidin-1-yl or piperidino etc., preferably amino, dimethylamino and diethylamino and particularly primary amino.

The term "halogen" signifies fluorine, chlorine, bromine or iodine and preferably fluorine, chlorine or bromine and particularly fluorine and chlorine.

The term "heteroarylalkyl" alone or in combination, signifies an alkyl group as previously defined in which one or several, preferably one hydrogen atom has been replaced by an heteroaryl group as previously defined.

The term "alkoxyalkyl" alone or in combination, signifies an alkyl or cycloalkyl group as previously defined in which one or several, preferably one hydrogen atom has been replaced by an alkoxy group as previously defined. Examples are methoxyethyl, ethoxymethyl, methoxypropyl and ethoxyethyl.

The term "hydroxyalkyl" alone or in combination, signifies an alkyl or cycloalkyl group as previously defined in which one or several, preferably one hydrogen atom has been replaced by a hydroxy group. Examples are hydroxyethyl, 2-hydroxypropyl and 3-hydroxypropyl.

Examples of pharmaceutically usable salts of the compounds of formula I are salts with physiologically compatible mineral acids such hydrochloric acid, sulfuric acid or phosphoric acid; or with organic acids such as methanesulfonic acid, acetic acid, trifluoroacetic acid, citric acid, fumaric acid, maleic acid, tartaric acid, succinic acid or salicylic acid. Preferred salts of compounds of formula I are hydrochloride salts, succinate salts and fumarate salts. Particularly preferred salts of compounds according to formula I are hydrochloride salts. The compounds of formula I can also form salts with physiologically compatible bases. Examples of such salts are alkali metal, alkali earth metal, ammonium and alkylammonium salts such as the Na, K, Ca or tetramethylammonium salt. The compounds of formula I can also be present in the form of zwitterions.

The invention expressly includes pharmaceutically acceptable derivatives of the compounds of formula I. For example hydroxy groups of compounds of formula I can be esterified. Examples of pharmaceutically acceptable esters of compounds according to formula I are formate, acetate, propionate, butyrate, isobutyrate, valerate, 2-methylbutyrate, isovalerate and N,N-dimethylaminoacetate. Preferred esters are acetate and N,N-dimethylaminoacetate.

Also included are pharmaceutically acceptable solvates of compounds according to formula I such as for example hydrates. The solvation can be effected in the course of the manufacturing process or can take place e.g. as a consequence of hygroscopic properties of an initially anhydrous compound of formula I (hydration).

The term "lipase inhibitor" refers to compounds that are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, *J. Antibiot.*, 47(12): 1369–1375 (1994)). The term "lipase inhibitor" refers also to polymer bound lipase inhibitors for example described in International Patent Application WO99/34786 (Geltex Pharmaceuticals Inc.). These polymers are characterised in that they have been substituted with one or more groups that inhibit lipases. The term "lipase inhibitor" also comprises pharmaceutically acceptable salts of these compounds. The term "lipase inhibitor" preferably refers to orlistat.

Orlistat is a known compound useful for the control or prevention of obesity and hyperlipidemiai. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 185,359, 189,577, 443,449, and 524,495.

Orlistat is preferably orally administered from 60 to 720 mg per day in divided doses two to three times per day. Preferred is wherein from 180 to 360 mg, most preferably 360 mg per day of a lipase inhibitor is administered to a subject, preferably in divided doses two or, particularly, three times per day. The subject is preferably an obese or overweight human, i.e. a human with a body mass index of 25 or greater. Generally, it is preferred that the lipase inhibitor be administered within about one or two hours of ingestion of a meal containing fat. Generally, for administering a lipase inhibitor as defined above it is preferred that treatment be administered to a human who has a strong family history of obesity and has obtained a body mass index of 25 or greater.

Orlistat can be administered to humans in conventional oral compositions, such as, tablets, coated tablets, hard and soft gelatin capsules, emulsions or suspensions. Examples of carriers which can be used for tablets, coated tablets, dragées and hard gelatin capsules are lactose, other sugars and sugar alcohols like sorbitol, mannitol, maltodextrin, or other fillers; surfactants like sodium lauryl sulfate, Brij 96, or Tween 80; disintegrants like sodium starch glycolate, maize starch or derivatives thereof; polymers like povidone, crospovidone; talc; stearic acid or its salts and the like. Suitable carriers for soft gelatin capsules are, for example, vegetable oils, waxes, fats, semi-solid and liquid polyols and the like. Moreover, the pharmaceutical preparations can contain preserving agents, solubilizers, stabilising agents, wetting agents, emulsifying agents, sweetening agents, colouring agents, flavouring agents, salts for varying the osmotic pressure, buffers, coating agents and antioxidants. They can also contain still other therapeutically valuable substances. The formulations may conveniently be presented in unit dosage form and may be prepared by any methods known in the pharmaceutical art. Preferably, orlistat is administered according to the formulation shown in the Examples and in U.S. Pat. No. 6,004,996, respectively.

In the nomenclature used in the present application the carbon atoms of the basic ring system of the compounds according to formula I are numbered as follows:

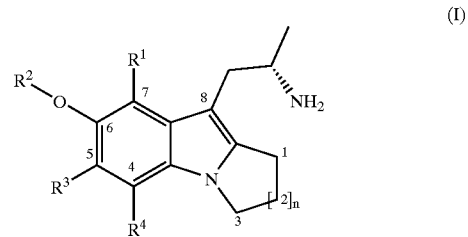

(I)

wherein $R^1$ is attached at the 7-position, $R^3$ is attached to the 5-position and $R^4$ is attached to the 4-position.

The compounds of formula I can contain several asymmetric centres and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant).

The term "asymmetric carbon atom (C*)" means a carbon atom with four different substituents. According to the Cahn-Ingold-Prelog-Convention the asymmetric carbon atom can be of the "R" or "S" configuration.

Chiral compounds of formula (I) are preferred,

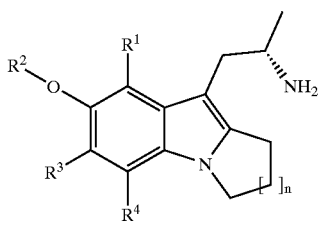
(I)

wherein $R^1$ to $R^4$ and n are defined as before. Formula (I) means that the asymmetric carbon atom C*

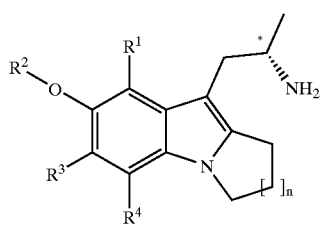

is of the S configuration.

Preferred are compounds of formula I and the pharmaceutically acceptable salts thereof.

In a preferred embodiment of the invention the term "optionally substituted with" as used in the definition of $R^2$ means that hydroxyalkyl and alkoxyalkyl can be substituted with one or two, preferably one substituent independently selected from trifluoromethyl, alkoxy or hydroxy.

Preferred are compounds of formula I, wherein $R^2$ is methyl, ethyl, cyclopropyl, aralkyl, heteroarylalkyl, alkoxyalkyl, 3-oxetanyl, 3-tetrahydrofuranyl, 2-tetrahydrofuranylmethyl, 3-tetrahydrofuranylmethyl or hydroxyalkyl, wherein hydroxyalkyl and alkoxyalkyl are optionally substituted with trifluoromethyl, alkoxy or hydroxy.

Preferred are compounds of formula I, wherein $R^2$ is methyl, ethyl, cyclopropyl, heteroarylalkyl, alkoxyalkyl, 3-oxetanyl, 3-tetrahydrofuranyl, 2-tetrahydrofuranylmethyl, 3-tetrahydrofuranylmethyl or hydroxyalkyl, wherein hydroxyalkyl and alkoxyalkyl are optionally substituted with trifluoromethyl, alkoxy or hydroxy.

More preferred are compounds of formula I, wherein $R^2$ is ethyl, cyclopropyl, aralkyl, heteroarylalkyl, alkoxyalkyl, 3-oxetanyl, 3-tetrahydrofuranyl, 2-tetrahydrofuranylmethyl, 3-tetrahydrofuranylmethyl or hydroxyalkyl, wherein hydroxyalkyl and alkoxyalkyl are optionally substituted with trifluoromethyl, alkoxy or hydroxy.

Likewise preferred are compounds of formula I, wherein $R^2$ is ethyl, cyclopropyl, alkoxyalkyl or hydroxyalkyl, wherein alkoxyalkyl is optionally substituted with alkoxy.

Particularly preferred are compounds of formula I, wherein $R^2$ is ethyl, methoxyethyl, cyclopropyl, hydroxyethyl, methoxypropyl, methoxybutyl, ethoxyethyl, ethoxypropyl, methoxyethoxyethyl, methoxyethoxypropyl or hydroxyethyl.

Most preferred are compounds of formula I, wherein $R^2$ is ethyl, 2-methoxyethyl, cyclopropyl, 2-hydroxyethyl, 3-methoxypropyl, 4-methoxybutyl, 2-ethoxyethyl, 3-ethoxypropyl, 2-(2-methoxy-ethoxy)-ethyl, 3-(2-methoxy-ethoxy)-propyl or hydroxyethyl.

Particularly preferred are compounds of formula I, wherein $R^2$ is ethyl.

Further particularly preferred are compounds of formula I, wherein $R^2$ is methoxypropyl.

Another preferred embodiment of the present invention are compounds of formula I, wherein n is 1 or 2. Particularly preferred are the compounds of formula I, wherein n is 1.

A further preferred aspect of the present invention are compounds of formula I, wherein $R^1$ is hydrogen.

Further preferred compounds of formula I are those wherein $R^1$ is fluoro.

Another preferred aspect of the present invention are compounds of formula I wherein $R^3$ is hydrogen.

Also preferred are compounds of formula I wherein $R^3$ is fluoro.

Preferred are compounds according to formula I wherein $R^4$ is hydrogen.

A particularly preferred compound of formula I is the compound (S)-2-(6-ethoxy-2,3-dihydro-1H-3a-aza-cyclopenta[a]inden-8-yl)-1-methyl-ethylamine.

A further particularly preferred compound of formula I is the compound (S)-2-[6-(2-methoxy-ethoxy)-2,3-dihydro-1H-3a-aza-cyclopenta[a]inden-8-yl]-1-methyl-ethyl amine.

Another particularly preferred compound of formula I is the compound (S)-2-(6-cyclopropoxy-2,3-dihydro-1H-3a-aza-cyclopenta[a]inden-8-yl)-1-methyl-ethylamine.

A further particularly preferred compound of formula I is the compound (S)-2-[8-(2-amino-propyl)-2,3-dihydro-1H-3a-aza-cyclopenta[a]inden-6-yloxy]-ethanol.

Yet another particularly preferred compound of formula I is the compound (S)-2-[6-(3-methoxy-propoxy)-2,3-dihydro-1H-3a-aza-cyclopenta[a]inden-8-yl]-1-methyl-ethylamine.

A further preferred embodiment of the invention is a compound selected from one of the following compounds
(S)-2-[6-(4-methoxy-butoxy)-2,3-dihydro-1H-3a-aza-cyclopenta[a]inden-8-yl]-1-methyl-ethylamine;
(S)-2-[6-(2-ethoxy-ethoxy)-2,3-dihydro-1H-3a-aza-cyclopenta[a]inden-8-yl]-1-methyl-ethylamine;
(S)-2-[6-(3-ethoxy-propoxy)-2,3-dihydro-1H-3a-aza-cyclopenta[a]inden-8-yl]-1-methyl-ethylamine;
(S)-2-{6-[2-(2-methoxy-ethoxy)-ethoxy]-2,3-dihydro-1H-3a-aza-cyclopenta[a]inden-8-yl}-1-methyl-ethylamine;
(S)-2-{6-[3-(2-methoxy-ethoxy)-propoxy]-2,3-dihydro-1H-3a-aza-cyclopenta[a]inden-8-yl}-1-methyl-ethylamine;
(S)-2-(6-ethoxy-5-fluoro-2,3-dihydro-1H-3a-aza-cyclopenta[a]inden-8-yl)-1-methyl-ethylamine;
(S)-2-[5-fluoro-6-(2-methoxy-ethoxy)-2,3-dihydro-1H-3a-aza-cyclopenta[a]inden-8-yl]-1-methyl-ethylamine;
(S)-2-[5-fluoro-6-(3-methoxy-propoxy)-2,3-dihydro-1H-3a-aza-cyclopenta[a]inden-8-yl]-1-methyl-ethyl amine;
(S)-2-[8-(2-amino-propyl)-5-fluoro-2,3-dihydro-1H-3a-aza-cyclopenta[a]inden-6-yloxy]-ethanol;
(S)-2-(6-ethoxy-7-fluoro-2,3-dihydro-1H-3a-aza-cyclopenta[a]inden-8-yl)-1-methyl-ethylamine;
(S)-2-(7-fluoro-6-methoxy-2,3-dihydro-1H-3a-aza-cyclopenta[a]inden-8-yl)-1-methyl-ethylamine;
(S)-2-[7-fluoro-6-(2-methoxy-ethoxy)-2,3-dihydro-1H-3a-aza-cyclopenta[a]inden-8-yl]-1-methyl-ethylamine;
(S)-2-[7-fluoro-6-(3-methoxy-propoxy)-2,3-dihydro-1H-3a-aza-cyclopenta[a]inden-8-yl]-1-methyl-ethylamine;
(S)-2-[8-(2-amino-propyl)-7-fluoro-2,3-dihydro-1H-3a-aza-cyclopenta[a]inden-6-yloxy]-ethanol; and
(S)-2-(6-cyclopropoxy-7-fluoro-2,3-dihydro-1H-3a-aza-cyclopenta[a]inden-8-yl)-1-methyl-ethylamine.

The hydrochloride salts of the compounds of formula I are preferred, particularly the hydrochloride salt of (S)-2-(6-ethoxy-2,3-dihydro-1H-3a-aza-cyclopenta[a]inden-8-yl)-1-methyl-ethylamine.

Processes for the manufacture of the compounds of formula I are an object of the present invention. The substituents and indices used in the following schemes have the significance given above unless indicated to the contrary.

Compounds of formula (I) where $R^1$ to $R^4$ and n are as previously defined may be conveniently prepared according to Scheme 1:

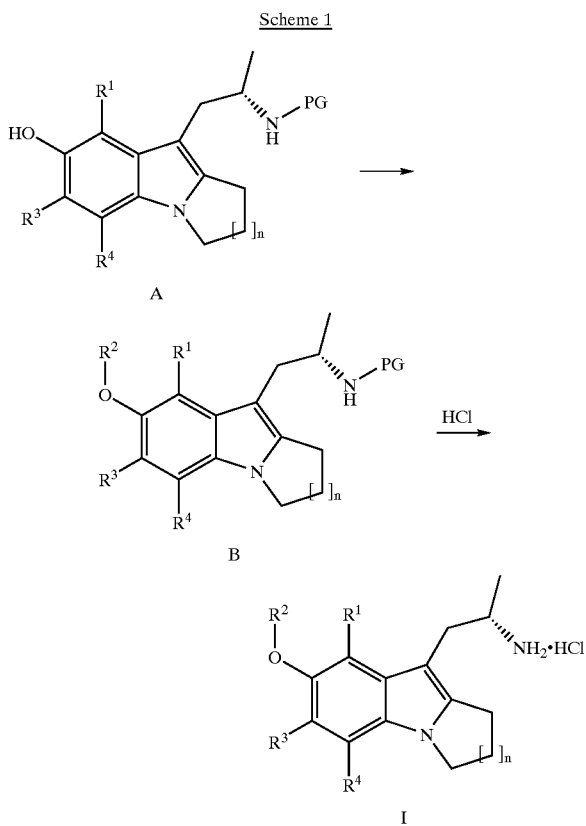

According to scheme 1, a phenol intermediate of formula A which is protected with a suitable protecting group (e.g. a tert-butoxycarbonyl (Boc) protecting group) on the amino group can be alkylated or acylated with suitable alkylating or acylating agents (X means for example Cl, Br or I) ($R^2$—X) in the presence of a base (e.g. sodium hydride) in a suitable inert solvent (e.g. DMSO, DMF or THF) to yield an intermediate of formula B. In a second step the protecting group is removed by methods known in the art to yield a compound of formula I (e.g. the Boc group is removed by acids preferably by hydrochloric acid in an inert solvent e.g. ethylacetate, dioxane or diethyl ether)

Functional groups $R^2$ that do not tolerate the method described for the synthesis of intermediate B can be prepared from such functional groups that do by methods known in the art (e.g. March, Advanced Organic Chemistry $4^{th}$. edition or Comprehensive Organic Functional Group Transformations, 1995). As an example the hydroxyethyl group can be introduced by first alkylating compound A with a suitable alpha halogen acetic acid ester followed by reduction of this ester with a suitable reducing agent to give an intermediate of formula B where $R^2$ is hydroxyethyl.

The processes as described above may be carried out to give a compound of the invention in the form of a free base or as an acid addition salt. If the compound of the invention is obtained as an acid addition salt, the free base can be obtained by basifying a solution of the acid addition salt. Conversely, if the product of the process is a free base, an acid addition salt, particularly a pharmaceutically acceptable acid addition salt, may be obtained by dissolving the free base in a suitable organic solvent and treating the solution with an acid, in accordance with conventional procedures for preparing acid addition salts from basic compounds.

A further object of the present invention is the process for the preparation of a compound according to formula I comprising the alkylation of an intermediate of formula C with a suitable alkylating agent ($R^2$—X) (X means for example Cl, Br or I) in the presence of a base (e.g. sodium hydride) in a suitable solvent (e.g. DMSO or DMF) to yield an intermediate of formula D. This intermediate D is then brominated or iodinated, preferably iodinated with suitable iodinating agents (e.g. N-Iodosuccinimide in a inert solvent e.g. acetonitrile) to yield an intermediate of formula E. This intermediate E is treated with an agent effecting halogen-metal exchange, preferably halogen-lithium exchange (e.g. with butyl-lithium in an inert solvent e.g. THF) and treated with the novel Sulfamidate F to yield an intermediate of formula B. This latter intermediate B is transformed to a compound of formula I as described before.

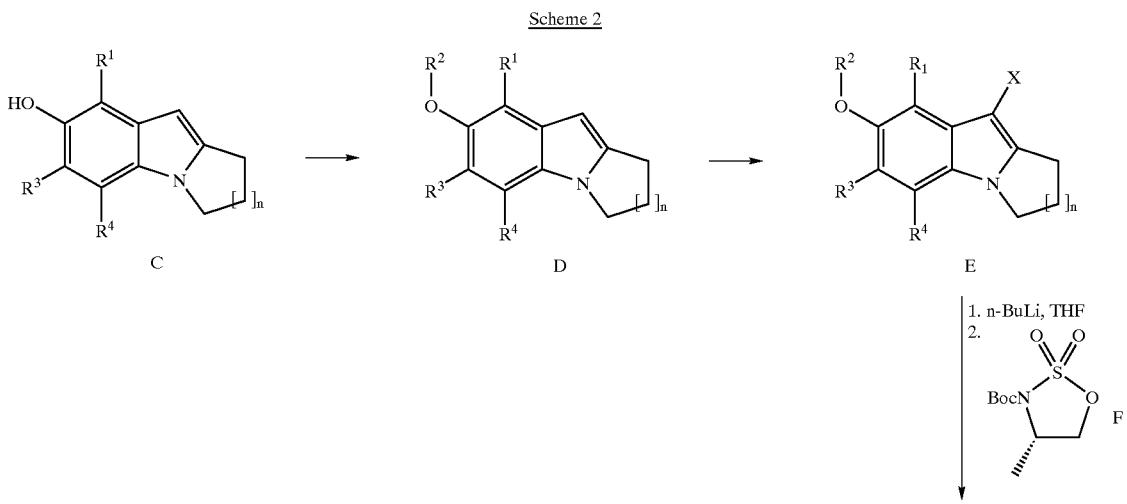

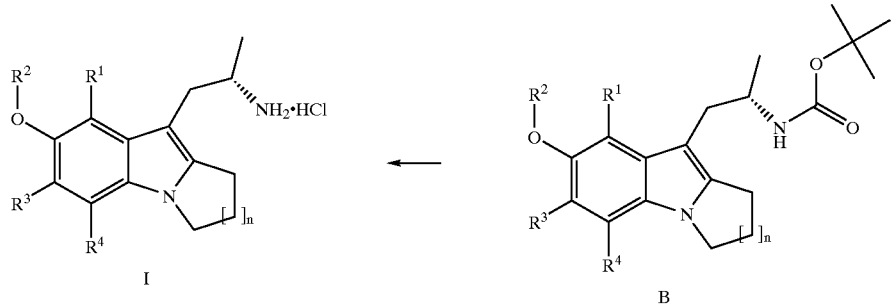

A compound of formula A where the protecting group is the Boc-protecting group can be conveniently prepared according to Scheme 3 in the following way:

A compound of formula C is protected with a suitable protecting group stable to the basic reaction media involved in the further elaboration to the intermediate A (e.g. C is protected with the thexyl group (1,1,2-trimethyl-propyl)-silanyl group) by reacting preferably thexyl chloride with C in the presence of a suitable base and in a inert solvent). The thus protected intermediate C is then subjected to the procedure as described for Scheme 2 to deliver after deprotection by methods known in the art (e.g. with ammonium fluoride in methanol) an intermediate of formula A where the protecting group PG is the Boc protecting group. Boc means a tert-butoxycarbonyl group.

A compound of formula C can be conveniently prepared according to Scheme 4 in the following way:

A suitably substituted p-bromo aniline is transformed into the methylcarbamate by reacting with methyl chloroformate in a suitable inert solvent (e.g. dichloromethane) in the presence of a base (e.g. aqueous sodium bicarbonate). The intermediate anilinocarbamate is then iodinated by methods known in the art (e.g. with N-iodosuccinimide (NIS) in an inert solvent e.g. acetonitrile in the presence of a Lewis or Bronsted acid e.g. trifluoromethanesulfonic acid (TfOH)). This iodinated intermediate is then subjected to a Sonogashira coupling reaction (Kondo, Yoshinori; Kojima, Satoshi; Sakamoto, Takao. General and Facile Synthesis of Indoles with Oxygen-Bearing Substituents at the Benzene Moiety. J. Org. Chem. (1997), 62(19), 6507–6511.) with a suitable chloro-alkyne (e.g. 5-chloro-1-pentyne) in a suitable solvent Scheme 3

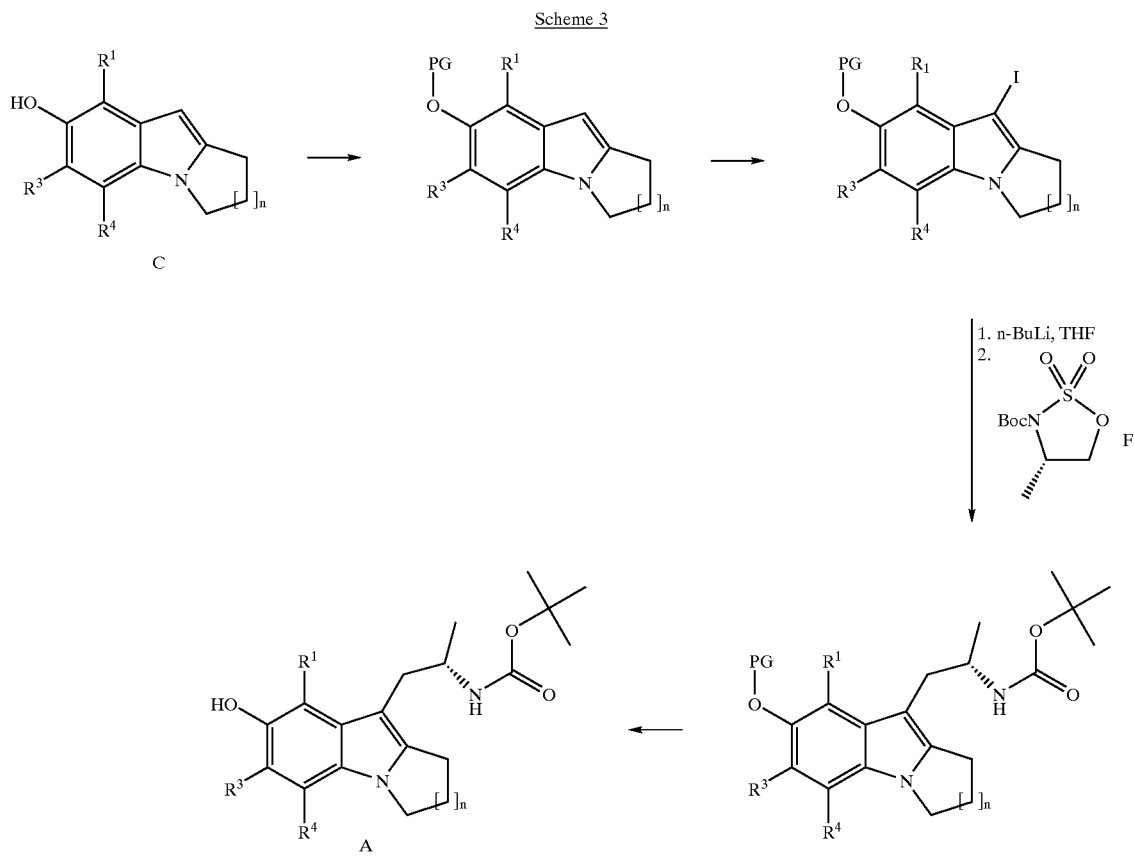

(e.g. triethylamine) in the presence of a metal catalyst or catalyst mixture (e.g. bis-(triphenylphosphine)-palladium (II)dichloride and copper(I)iodide). The Sonogashira coupling product is transformed to the tricyclic indole G by the action of suitable bases (e.g. alkali metal hydroxide in particular lithium hydroxide) in a suitable inert solvent (such as tert-butanol or DMSO). The intermediate G is transformed into C by halogen metal exchange, preferably with butyl lithium in an inert solvent, preferably THF followed by reaction with a suitable trialkylborate, preferably triisopropylborate and oxidation of the resulting boronic acid derivative with hydrogen peroxide.

Scheme 4

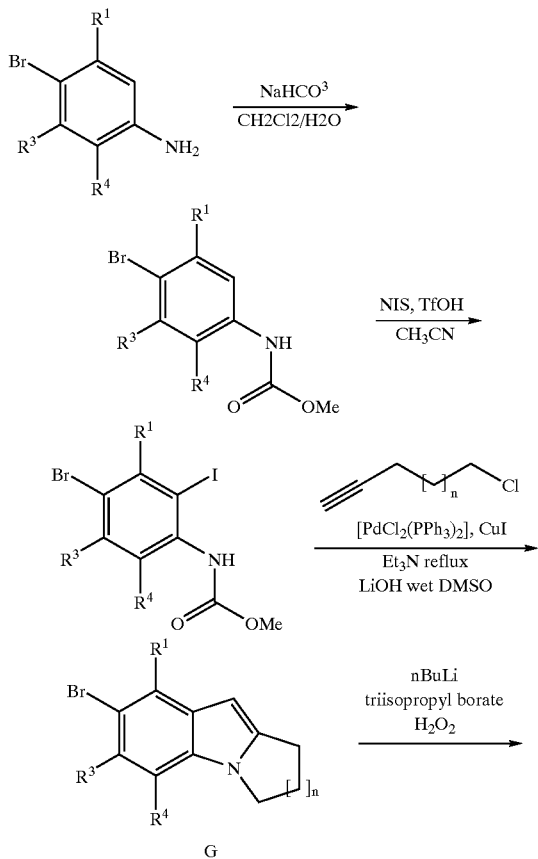

A suitably substituted p-aminophenol is transformed into an intermediate of formula H by reacting with methyl chloroformate in a suitable inert solvent (e.g. THF) in the presence of a base (e.g. triethylamine) The intermediate H is then iodinated by methods known in the art (e.g. with N-iodosuccinimide in an inert solvent e.g. acetonitrile in the presence of a Lewis or Bronsted acid (e.g. trifluoromethanesulfonic acid). This iodinated intermediate is then subjected to a Sonogashira coupling reaction with a suitable chloroalkyne (e.g. 5-chloro-1-pentyne) in a suitable solvent or solvent mixture (e.g. triethylamine and acetonitrile) in the presence of a metal catalyst or catalyst mixture (e.g. bis-(triphenylphosphine)-palladium(II)dichloride and copper(I) iodide). The product of the Sonogashira reaction is then mono-deprotected with a suitable base (e.g. ammonia) in a suitable inert solvent (e.g. THF) to yield the phenol which is alkylated or acylated by suitable alkylating agents $R^2$—X (X means for example Cl, Br or I) in an inert solvent (e.g. DMF) in the presence of a suitable base (e.g. potassium carbonate). Ring closure to the intermediate D is achieved in two steps: first treatment with a catalyst (e.g. palladium (II) chloride) in an inert solvent (e.g. acetonitrile) at elevated temperatures; then treatment of the intermediate indole with a base (e.g. potassium hydroxide) in an inert solvent (e.g. tert-butanol) at an elevated temperature.

Scheme 5

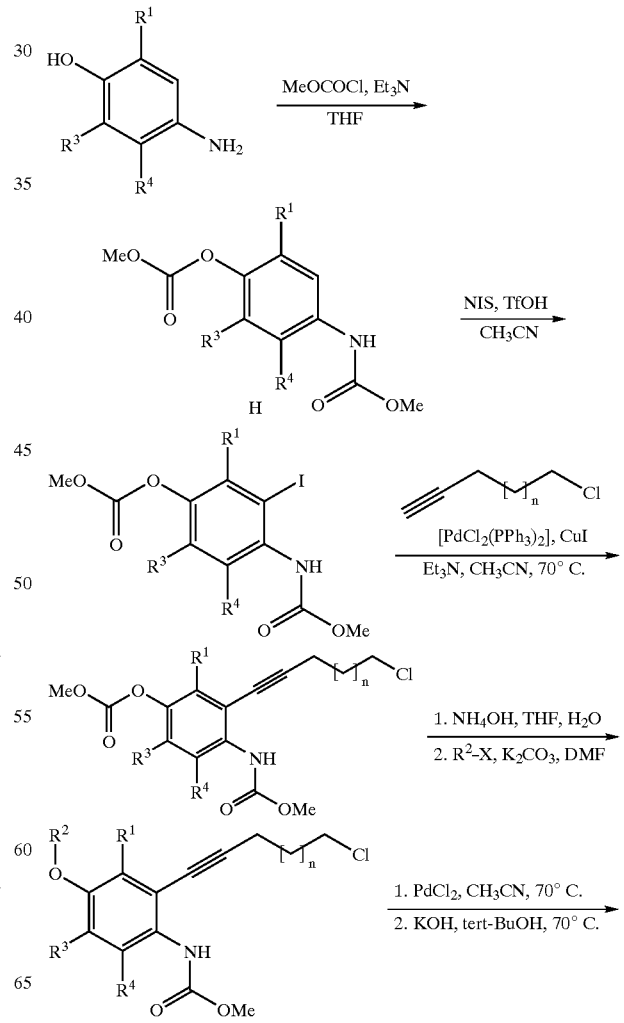

A compound of formula D can be conveniently prepared according to Scheme 5 in the following way:

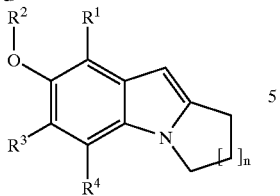

D

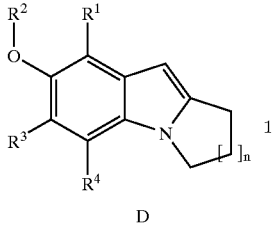

D

A further preferred embodiment of the present invention is the process for the preparation of a compound of formula I comprising deprotecting a compound of formula B,

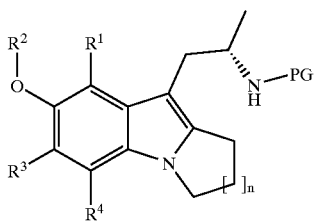

B wherein $R^1$ to $R^4$ and n are defined as before and PG means a protecting group. This process is particularly preferred for the preparation of salts of compounds of formula I such as hydrochloride salts. An example of a suitable protecting group PG is the tert-butoxycarbonyl (Boc) protecting group. The Boc group can be removed by methods known in the art such as treatment with an acid preferably hydrochloric acid, trifluoroacetic acid and mixtures of trifluoroacetic acid and inert solvents such as dichloromethane.

A further object of the invention are compounds of formula I, when manufactured according to the above process.

Another preferred embodiment of the present invention is the following intermediates:

Compounds of formula E where X means bromo or iodo preferably iodo as described in scheme 2.

Scheme 6

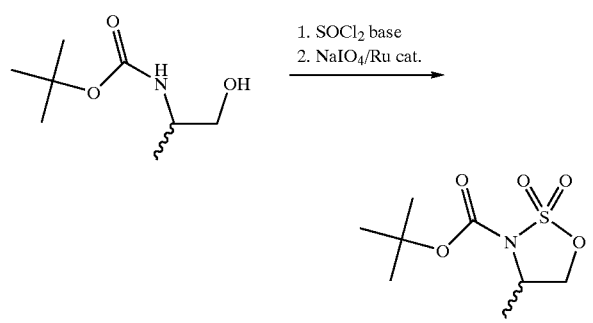

1. SOCl₂ base
2. NaIO₄/Ru cat.

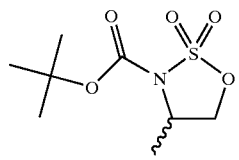

The intermediates of formula P can be conveniently prepared according to Scheme 6 from N-Boc-alaninol by reaction with thionylchloride in an inert solvent such as tetrahydrofuran or dichloromethane in the presence of a suitable base such as n-butyllithium, triethylamine or imidazole and then oxidation of the intermediate sulfamidite with a suitable oxidising agent such as sodium metaperiodate in the presence of a suitable catalyst such as ruthenium dioxide or ruthenium trichloride.

It is a further object of the invention to provide compounds of formula I for use as therapeutically active substances.

It is another object of the invention to provide compounds of formula I as described above for the production of pharmaceutical compositions for the prophylaxis and therapy of illnesses which are caused by disorders associated with the 5-HT₂ receptors, particularly with the 5-HT$_{2A}$, 5-HT$_{2B}$ and 5-HT$_{2C}$ subtypes. Most preferred is the 5-HT$_{2C}$ subtype.

Likewise it is an object of the invention to provide pharmaceutical compositions comprising a compound of formula I and a therapeutically inert carrier.

It is a further object of the invention to provide a compound in accordance with formula I for use in the production of pharmaceutical compositions for the treatment and prophylaxis of eating disorders and obesity.

Also preferred is the use of a compound in accordance with formula I for the production of pharmaceutical compositions for the treatment and prophylaxis of diabetes mellitus (DM) including Type I diabetes (insulin dependent diabetes mellitus (IDDM)), Type II diabetes (non-insulin dependent diabetes mellitus (NIDDM)), diabetes secondary to pancreatic disease, diabetes related to steroid use, Type III diabetes (malnutrition related diabetes), diabetes insipidus, hyperglycaemia, diabetic complications and insulin resistance.

Particularly preferred is a method of treatment comprising administering an effective amount of a compound in accordance with formula I for the production of pharmaceutical compositions for the treatment and prophylaxis of diabetes mellitus (DM) including Type I diabetes (insulin dependent diabetes mellitus (IDDM)), Type II diabetes (non-insulin dependent diabetes mellitus (NIDDM)), diabetes secondary to pancreatic disease, diabetes related to steroid use, Type III diabetes (malnutrition related diabetes), hyperglycaemia, diabetic complications and insulin resistance.

It is a further particularly preferred object of the invention to provide a compound of formula I for use in the production of pharmaceutical compositions for the treatment and prophylaxis of Type II diabetes (non-insulin dependent diabetes mellitus (NIDDM)).

An object of the invention is the use of compounds of formula I for the production of pharmaceutical compositions for the treatment and prophylaxis of disorders of the central nervous system, cardiovascular disorders, gastrointestinal disorders and sleep apnoea.

Particularly an object of the invention is the above method of treatment, wherein the disorders of the central nervous system are selected from depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioural disorders, behavioural disorders associated with dementia, organic mental disorders, mental disorders in childhood, aggressivity, age-related memory disorders, chronic fatigue syndrome, drug and alcohol addiction, bulimia, anorexia nervosa, premenstrual tension, trauma, stroke, neurodegenerative diseases, encephalitis and meningitis.

A further preferred embodiment of the present invention is the above mentioned method of treatment compounds of formula I, wherein the cardiovascular disorder is thrombosis.

Also preferred is the aforementioned use of the compounds of formula I, wherein the gastrointestinal disorder is dysfunction of gastrointestinal motility.

A further object of the invention are compounds of formula I, when manufactured according to the processes described herein.

A further embodiment of the present invention is a method for the treatment and prophylaxis of disorders of the central nervous system, cardiovascular disorders, gastrointestinal disorders and sleep apnoea, which method comprises administering an effective amount of a compound of formula I as described.

Preferred is this method, wherein the disorders of the central nervous system are selected from depression, atypical depression, bipolar disorders, anxiety disorders, obsessive-compulsive disorders, social phobias or panic states, sleep disorders, sexual dysfunction, psychoses, schizophrenia, migraine and other conditions associated with cephalic pain or other pain, raised intracranial pressure, epilepsy, personality disorders, age-related behavioural disorders, behavioural disorders associated with dementia, organic mental disorders, mental disorders in childhood, aggressivity, age-related memory disorders, chronic fatigue syndrome, drug and alcohol addiction, bulimia, anorexia nervosa, premenstrual tension, trauma, stroke, neurodegenerative diseases, encephalitis and meningitis.

Preferred is a method for the treatment and prophylaxis of of diabetes mellitus (DM), Type I diabetes (insulin dependent diabetes meeitus (IDDM)), Type II diabetes (non-insulin dependent diabetes mellitus (NIDDM)), diabetes secondary to pancreatic disease, diabetes related to steroid use, type III diabetes (malnutrition related diabetes), diabetes insipidus, hyperglycemia, diabetic complications and insulin resistance, which method comprises administering an effective amount of a compound in accordance with formula I to a person in need of such treatment.

Particularly preferred is a method for the treatment and prophylaxis of of diabetes mellitus (DM), Type I diabetes (insulin dependent diabetes meeitus (IDDM)), Type II diabetes (non-insulin dependent diabetes mellitus (NIDDM)), diabetes secondary to pancreatic disease, diabetes related to steroid use, type III diabetes (malnutrition related diabetes), hyperglycemia, diabetic complications and insulin resistance, which method comprises administering an effective amount of a compound in accordance with formula I to a person in need of such treatment.

It is a preferred object of the invention to provide a method for the treatment and prophylaxis of eating disorders and obesity, which method comprises administering an effective amount of a compound of formula I to a person in need of such treatment.

It is a preferred object of the invention to provide a method for the treatment and prophylaxis of Type II diabetes (non-insulin dependent diabetes mellitus (NIDDM), which method comprises administering an effective amount of a compound of formula I to a person in need of such treatment.

It is a further preferred object of the invention to provide a method of treatment of obesity in a human which comprises administration of a therapeutically effective amount of a compound according to formula I and a therapeutically effective amount of a lipase inhibitor, particularly, wherein the lipase inhibitor is orlistat. Also an object of the invention is the method as described above for the simultaneous, separate or sequential administration.

It is a further preferred object to provide a method of treatment of Type II diabetes (non-insulin dependent diabetes mellitus (NIDDM) in a human which comprises administration of a therapeutically effective amount of a compound according to formula I and a therapeutically effective amount of a lipase inhibitor, particularly, wherein the lipase inhibitor is orlistat. Also an object of the invention is the method as described above for the simultaneous, separate or sequential administration of a compound according to formula I and a lipase inhibitor, particularly orlistat.

It is a further preferred object of the invention to provide a method of treatment of diabetes mellitus (DM), Type I diabetes (insulin dependent diabetes mellitus (IDDM)), Type II diabetes (non-insulin dependent diabetes mellitus (NIDDM)), diabetes secondary to pancreatic disease, diabetes related to steroid use, Type III diabetes (malnutrition related diabetes), diabetes insipidus, hyperglycaemia, diabetic complications and insulin resistance in a human which comprises administration a therapeutically effective amount of a compound according to formula I and a therapeutically effective amount of a lipase inhibitor, particularly, wherein the lipase inhibitor is orlistat. It is also an object of the invention to provide a method as described above for the simultaneous, separate or sequential administration of a compound according to formula I and a lipase inhibitor, particularly orlistat.

It is a further particularly preferred object of the invention to provide a method of treatment of diabetes mellitus (DM), Type I diabetes (insulin dependent diabetes mellitus (IDDM)), Type II diabetes (non-insulin dependent diabetes mellitus (NIDDM)), diabetes secondary to pancreatic disease, diabetes related to steroid use, Type III diabetes (malnutrition related diabetes), hyperglycaemia, diabetic complications and insulin resistance in a human which comprises administration a therapeutically effective amount of a compound according to formula I and a therapeutically effective amount of a lipase inhibitor, particularly, wherein the lipase inhibitor is orlistat. It is also an object of the invention to provide a method as described above for the simultaneous, separate or sequential administration of a compound according to formula I and a lipase inhibitor, particularly orlistat.

A further object of the invention is the use of a compound of formula I in the manufacture of a medicament for the treatment and prevention of obesity in a patient who is also receiving treatment with a lipase inhibitor and particularly, wherein the lipase inhibitor is orlistat.

A further object of the invention is the use of a compound of formula I in the manufacture of a medicament for the treatment and prevention of Type II diabetes (non-insulin dependent diabetes mellitus (NIDDM)) in a patient who is also receiving treatment with a lipase inhibitor and particularly, wherein the lipase inhibitor is orlistat.

A further preferred object of the present invention is the use of a compound according to formula I in the manufacture of a medicament for the treatment and prevention of diabetes mellitus (DM), Type I diabetes (insulin dependent diabetes mellitus (IDDM)), Type II diabetes (non-insulin dependent diabetes mellitus (NIDDM)), diabetes secondary to pancreatic disease, diabetes related to steroid use, Type III diabetes (malnutrition related diabetes), diabetes insipidus, hyperglycaemia, diabetic complications and insulin resistance in a patient who is also receiving treatment with a lipase inhibitor particularly, wherein the lipase inhibitor is orlistat.

A further particularly preferred object of the present invention is the use of a compound according to formula I in the manufacture of a medicament for the treatment and prevention of diabetes mellitus (DM), Type I diabetes (insulin dependent diabetes mellitus (IDDM)), Type II diabetes (non-insulin dependent diabetes mellitus (NIDDM)), diabetes secondary to pancreatic disease, diabetes related to steroid use, Type III diabetes (malnutrition related diabetes), hyperglycaemia, diabetic complications and insulin resistance in a patient who is also receiving treatment with a lipase inhibitor particularly, wherein the lipase inhibitor is orlistat.

It is also an object of the invention to provide a pharmaceutical composition comprising a compound of formula I, a therapeutically inert carrier and further a therapeutically effective amount of a lipase inhibitor, particularly, wherein the lipase inhibitor is orlistat.

It is also a preferred object of the invention to provide a method of treatment and/or prevention in mammals disorders where a reduction of the blood glucose concentration is beneficial comprising administering a therapeutically effective amount of a compound of formula I. Particularly preferred is this use or method wherein the disorders are disorders involving elevated plasma blood glucose.

The compounds of formula (I) may be used in the treatment (including prophylactic treatment) of disorders associated with 5-$HT_2$ receptor function. The compounds may act as receptor agonists or antagonists. Preferably, the compounds may be used in the treatment (including prophylactic treatment) of disorders associated with 5-$HT_{2B}$ and/or 5-$HT_{2C}$ receptor function. Preferably, the compounds may be used in the treatment (including prophylactic treatment) of disorders where a 5-$HT_{2C}$ receptor agonist is required.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) transdermal or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropylmethylcellulose); fillers (e.g. lactose, microcrystalline cellulose or calcium phosphate); lubricants (e.g. magnesium stearate Stearinic acid, Sotalc or silica); disintegrants (e.g. potato starch or sodium starch glycollate); or wetting agents (e.g. sodium lauryl sulfate), binders (e.g. Crospovidone, N-methyl pyrrolidone). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending/viscosity enhancing agents (e.g. sorbitol syrup, methyl cellulose or hydrogenated edible fats); emulsifying agents (e.g. lecithin or acacia); non-aqueous vehicles (e.g. almond oil, oily esters or ethyl alcohol, medium chain triglycerides); and preservatives (e.g. methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulating agents such as suspending, stabilizing and/or dispersing agents.

Alternatively, the active ingredient may be in powder form for reconstitution with a suitable vehicle, e.g. sterile pyrogen-free water, before use.

The active compounds of the invention may also be formulated in rectal compositions such as suppositories or retention enemas, e.g., containing conventional suppository bases such as cocoa butter, polyethylene glycoles, or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g. dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder for inhalation base such as lactose or starch.

A proposed dose of the active compounds of the invention for oral, parenteral or buccal administration to the average adult human for the treatment of the conditions referred to above (e.g., obesity) is 0.1 to 500 mg of the active ingredient per unit dose which could be administered, for example, 1 to 4 times per day.

The invention will now be described in detail with reference to the following examples. It will be appreciated that the invention is described by way of example only and modification of detail may be made without departing from the scope of the invention.

Assay Procedures

1. Binding to Serotonin Receptors

The binding of compounds of formula (I) to serotonin receptors was determined in vitro by standard methods. The preparations were investigated in accordance with the assays given hereinafter.

Method (a): For the binding to the 5-$HT_{2C}$ receptor the 5-$HT_{2C}$ receptors were radiolabeled with [$^3$H]-5-HT. The affinity of the compounds for 5-$HT_{2C}$ receptors in a CHO cell line was determined according to the procedure of D. Hoyer, G. Engel and H. O. Kalkman, *European J. Pharmacol.*, 1985, 118, 13–23.

Method (b): For the binding to the 5-HT$_{2B}$ receptor the 5-HT$_{2B}$ receptors were radiolabeled with [$^3$H]-5-HT. The affinity of the compounds for human 5-HT$_{2B}$ receptors in a CHO cell line was determined according to the procedure of K. Schmuck, C. Ullmer, P. Engels and H. Lubbert, *FEBS Lett.*, 1994, 342, 85–90.

Method (c): For the binding to the 5-HT$_{2A}$ receptor the 5-HT$_{2A}$ receptors were radiolabeled with [$^{125}$I]-DOI. The affinity of the compounds for 5-HT$_{2A}$ receptors in a CHO cell line was determined according to the procedure of D. J. McKenna and S. J. Peroutka, *J. Neurosci.*, 1989, 9, 3482–90.

The thus determined activity of the compounds of formula 1 are shown in Table 1. The activity is displayed as a calculated activity constant Ki. The Ki values are calculated according to the method of Cheng, Yung-Chi, and Prusoff, W. H. Biochem. Pharmacol. 1973, 22(23) 3099–108.

TABLE 1

| Compound | Method (a) Ki (2C) | Method (b) Ki (2B) | Method (c) Ki (2A) |
| --- | --- | --- | --- |
| Example 1 | 11 nM | 830 nM | 410 nM |
| Example 2 | 19 nM | 480 nM | 520 nM |

Preferred Ki (2C) values are below 1000 nM; especially preferred Ki (2C) values are below 100 nM, particularly preferred Ki (2C) values are below 50 nM. Most preferred Ki (2C) values are below 30 nM.

2. Functional Activity

The functional activity of compounds of formula (I) was assayed using a Fluorimetric Imaging Plate reader (FLIPR). CHO cells expressing the human 5-HT$_{2C}$ or human 5-HT$_{2A}$ receptors were counted and plated into standard 96 well microtitre plates on the day before testing to give a confluent monolayer. The cells were then dye loaded with the calcium sensitive dye, Fluo-3-AM. Unincorporated dye was removed using an automated cell washer to leave a total volume of 100 µL/well of assay buffer (Hanks balanced salt solution containing 20 mM Hepes and 2.5 mM probenecid). The drug (dissolved in 50 µL of the assay buffer) was added at a rate of 70 µL/sec to each well of the FLIPR 96 well plate during fluorescence measurements. The measurements were taken at 1 sec intervals and the maximum fluorescent signal was measured (approx 10–15 secs after drug addition) and compared with the response produced by 10 µM 5-HT (defined as 100%) to which it was expressed as a percentage response (relative efficacy). Dose response curves were constructed using Graphpad Prism (Graph Software Inc.).

The thus determined activity of the compounds of formula 1 are shown in Table 2.

TABLE 2

| | h5-HT$_{2C}$ | | h5-HT$_{2A}$ | |
| --- | --- | --- | --- | --- |
| Compound | EC$_{50}$ (nM) | Relative Efficacy (%) | EC$_{50}$ (nM) | Relative Efficacy (%) |
| Example 1 | | 87% | | 33% |
| Example 3 | 3 | 84% | >1000 | —% |

The compounds of formula (I) have activity at the h5-HT$_{2C}$ receptor in the range of 10,000 to 0.1 nM.

Preferred activities at the h5-HT$_{2C}$ receptor are below 1000 nM; especially preferred below 100 nM, particularly preferred activities are below 50 nM. Most preferred activity at the h5-HT$_{2C}$ receptor are below 30 nM.

The compounds of formula (I) have maximum functional activity at the h5-HT$_{2C}$ receptor in the range of 0 to 100%.

Preferred maximal functional activity at the h5-HT$_{2C}$ receptor as described above are above 50%; Most preferred maximal functional activity at the h5-HT$_{2C}$ receptor are above 70%.

3. Regulation of Feeding Behaviour

The in vivo activity of compounds of formula (1) was assayed for ability to regulate feeding behaviour by assaying food consumption in food deprived animals as follows.

Test compounds are assessed following acute administration. Each study utilises a between-subjects design (typically n=8) and compares the effects of doses of the test agent to those of vehicle and a positive control.

The anorectic drug d-fenfluramine normally serves as a positive control. The route of drug administration, drug volume and injection-test-interval are dependent upon the compounds used. A palatable wet mash, made by adding powdered lab chow and water in a ration of 1:2 and mixing to a smooth consistency, is presented in 120 mL glass jars for 60 minutes each day. Intake is measured by weighing before and after each session. Care is taken to collect all spillage. Animals are allowed to habituate to the wet mash meal for 10 days. After drug administration, animals are allowed to consume the wet mash. Food consumption is assayed at pre-determined time points (typically, 1, 2 and 4 hours after administration). Food intake data are subjected to one-way analysis of variance (ANOVA) with drug as a between-subjects factor. A significant main effect is followed up by the performance of Dunnett's test in order to assess which treatment mean(s) are significantly different from the control mean. All statistical analyses were performed using Statistica Software, Version 5.0 (Statsoft Inc.) and Microsoft Excel 7.0 (Microsoft Corp.).

The thus determined activity of the Examples indicated that the compounds maintain significant hypophagia 3 hours after a dose of 30 mg/kg per os. The thus determined activity of Example 1 indicate that the compound maintained significant hypophagia 1 hours after a dose of 10 mg/kg p.o. to rats.

4. Pharmacodynamic Study of Compounds of Formula (I)

The in vivo activity of compounds of formula (I) was assayed for ability to regulate feeding behaviour during a time period up to 16 hours after compound administration.

The test compound was assessed following acute administration. Each study utilised a between-subjects design (typically n=8) and compared the effects of a single dose of the test agent to those of vehicle.

Example 1 was administered at a dose of 30 mg/kg p.o. in a distilled water vehicle 2, 4, 8, or 16 hours prior to food presentation. At the time of food presentation (standard laboratory chow) all animals had been subjected to a 23-hour food deprivation period. Water was freely available throughout the study. The amount of food consumed over 1 hour was determined. Food intake data were subjected to two-way analysis of variance (ANOVA) with drug treatment as a between-subjects factor and injection-test-interval as a between subjects factor. Newman-Keuls tests were performed to assess whether differences between the vehicle mean and the drug-treated mean at each level of injection-test-interval were significant. All statistical analyses were performed using Statistica Software, Version 5.0 (Statsoft Inc.) and Microsoft Excel 7.0 (Microsoft Corp.).

Treatment with Example 1 led to a significant reduction in food intake in 23-hour food deprived rats even when the compound was administered up to 16 hours before food re-presentation.

The assay demonstrated that Example 1 has a duration of action of at least 16 hours in reducing rat food intake.

5. Regulation of Body Weight by Compounds of Formula (I)

The in vivo activity of compounds of formula (I) was assayed for ability to regulate body weight (BW) and blood glucose measured during an oral glucose tolerance test (OGTT).

Sprague-Dawley rats (approx. 10 weeks of age), fed with a high fat Diet (43% of energy) for 17 days became obese and diabetic. These so-called DIO rats (Diet-Induced Obesity) were treated twice daily with compounds given orally. A second group of rats was fed with chow diet and therefore did not put on weight. These lean control rats did not receive any treatment, but helped in comparing the BW evolution with that of DIO rats treated with placebo.

Each study utilised a between-subjects design (typically n=7 to 9) and compared the effects of the test agent to those of vehicle and a positive control, typically sibutramine.

The effects of the drug (administered daily as food admix) on BW was evaluated daily for the duration of the experiment. At the end of the treatment, animals were fasted overnight. An oral glucose tolerance test (OGTT, glucose challenge: 1 g/kg body weight) was then performed. A blood sample was taken prior to glucose injection (fasting blood glucose), then 5 times after glucose was injected (typically, at 5, 20, 40, 60 and 120 minutes). The effects of drug on BW and glucose (measured during the OGTT) were evaluated. Data were subjected to one-way analysis of variance (ANOVA) with drug treatment as a between-subjects factor. A significant main effect is followed up by the performance of T-test in order to assess which treatment mean(s) are significantly different from the control mean. All statistical analyses were performed using Statview Software, and Microsoft Excel 7.0 (Microsoft Corp.).

17 days treatment with Example 1 (30 mg/kg per day as food admix) led to a significant reduction in BW. Mean fasting and non-fasting blood glucose measured during OGTT, at the end of the treatment were significantly decreased after 2 weeks of treatment compared to placebo-treated animals.

6. Modulation of Glucose Measured During OGTT by Compounds of Formula (I)

The in vivo activity of compounds of formula (I) was assayed for ability to regulate glucose utilisation in food deprived animals submitted to oral glucose tolerance test (OGTT) as follows.

The test compounds were assessed following acute and sub-chronic administration (1-week). Each study utilised a between-subjects design (typically n=5) and compared the effects of the test agent to those of vehicle.

Animals (rats, normal or diabetic) were housed 2 per cage and deprived of food but not water. Fasting blood glucose and body weight under non-fasting conditions are measured before drug's injection and used to establish homogeneous groups of animals. For acute test, the drug was given orally 2 hours-prior to glucose (1 g/kg body weight). Blood samples were taken at 5 time-points after glucose injection, typically at 5, 20, 40, 60, 120 minutes. For 1-week treated animals, drug was administered twice daily. OGTT was performed before starting the treatment and redone after completion of the treatment in the same animals. Blood glucose and plasma insulin concentrations are subjected to one-way analysis of variance (ANOVA) with drug as a between-subjects factor. A significant main effect on glucose or insulin concentration is followed up by the performance of T-test. All statistical analyses were performed using Statview Software, and Microsoft Excel 7.0 (Microsoft Corp.).

Treatment with the compound of Example 1 given acutely at 3 and 10 mg/kg (p.o.) significantly improves glucose utilization following oral glucose challenge compared to placebo-treated rats.

Example 1 given sub-chronically at 5 mg/kg twice daily (p.o.), significantly improves fasting blood glucose and glucose concentration measured during OGTT compared to rats of the same group tested before starting the treatment. Blood parameters are significantly improved compared to those of placebo-treated animals measured at the end of the treatment duration.

EXAMPLES

Example 1

Preparation of (S)-2-(6-ethoxy-2,3-dihydro-1H-3a-aza-cyclopenta[a]inden-8-yl)-1-methyl-ethylamine Route A: Synthesis from 4-aminophenol a) Carbonic acid 4-methoxycarbonylamino-phenyl ester methyl ester Triethylamine (33.46 mL, 0.24 mol) was added to a stirred suspension of 4-aminophenol (10.92 g, 0.10 mol) in tetrahydrofuran (450 mL). The mixture was cooled to 0° C. (ice-bath) and a solution of methyl chloroformate (16.15 mL, 0.21 mol) in tetrahydrofuran (70 mL) added dropwise over 50 min. The cooling bath was removed and the mixture stirred at room temperature overnight. The mixture was poured into 1M pH4 phosphate buffer (500 mL) and the phases separated. The aqueous phase was extracted with ethyl acetate (250 mL), the combined organic phases washed with brine, dried over sodium sulfate and evaporated. The combined residues from two runs were purified by column chromatography on silica gel (1 kg, 3:2 hexane/ethyl acetate eluant) to afford the product as a white solid (40 g, 88%). m.p. 75–76° C.

b) Carbonic acid 3-iodo-4-methoxycarbonylamino-phenyl ester methyl ester

A mixture of carbonic acid 4-methoxycarbonylamino-phenyl ester methyl ester (20.0 g, 88.8 mmol) and N-iodosuccinimide (23.8 g, 105.78 mmol) in acetonitrile (330 mL) was cooled to 0° C. (ice-bath). Trifluoromethane-sulfonic acid (1.6 mL, 18.2 mmol) was added dropwise. The cooling bath was removed and the reaction stirred 72 h at room temperature. TLC showed the reaction was complete. The mixture was poured into 1M pH7 phosphate buffer, and washed with ethyl acetate. The phases were separated, the aqueous phase was extracted with ethyl acetate and the combined organic phases washed with 10% sodium thiosulfate solution, brine, dried over sodium sulfate and evaporated. The residue was purified by column chromatography on silica gel (500 g, 3:2 hexane/ethyl acetate eluant) to afford the product as an off-white solid (28.7 g, 92%), which was used without further purification. m.p. 106° C.

c) Carbonic acid 3-(5-chloro-pent-1-ynyl)-4-methoxycarbonylamino-phenyl ester methyl ester Carbonic acid 3-iodo-4-methoxycarbonylamino-phenyl ester methyl ester (28.0 g, 79.75 mmol) was dissolved in acetonitrile (350 mL). Triethylamine (22.2mL, 160 mmol), Copper (I) iodide (300 mg, 1.58 mmol), bis(triphenylphosphine)palladium (II) chloride (1.12 g, 1.6 mmol) and 5-chloro-1-pentyne (10.0 mL, 95.54 mmol) were added and the mixture heated 3 h at 70° C. The reaction was cooled and partitioned between ethyl acetate (100 mL) and IM pH4 phosphate buffer (100 mL). The phases were separated, the aqueous phase extracted with ethyl acetate and the combined organic phases washed with 10% sodium thiosulfate solution, brine, dried over sodium sulfate and evaporated. The orange/brown residue (23.5 g, 90%) was used without further purification. (A small sample was purified by column chromatography on silica gel (5:1 hexane/ethyl acetate) for analytical purposes). ISP-MS: m/e=326.3 ([M–H]$^+$)

d) 2-(5-Chloro-pent-1-ynyl)-4-hydroxy-phenyl]-carbamic acid methyl ester

Carbonic acid 3-(5-chloro-pent-1-ynyl)-4-methoxycarbonylamino-phenyl ester methyl ester was dissolved in tetrahydrofuran (600 mL) and concentrated ammonium hydroxide (25%, 30 mL) in water. The mixture was stirred 4 h at 60° C. The reaction was not complete, and more concentrated ammonia (25%, 20 mL) was added and the mixture heated at 60° C. overnight. The mixture was cooled and evaporated under reduced pressure to half its volume, poured into IM pH4 phosphate buffer. The phases were separated, the aqueous phase extracted twice with ethyl acetate and the combined organic phases washed with brine, dried over sodium sulfate and evaporated. The resulting orange oil (26 g) was used without further purification. EI-MS: m/e=267.0 ([M]$^+$)

e) 2-(5-Chloro-pent-1-ynyl)-4-ethoxy-phenyl]-carbamic acid methyl ester

Iodoethane (15.8 mL, 220.64 mmol) and potassium carbonate (28.4 g, 220.05 mmol) were added to [2-(5-Chloro-pent-1-ynyl)-4-hydroxy-phenyl]-carbamic acid methyl ester (39 g, 145.68 mmol) in N,N-dimethylformamide (300 mL). The mixture was stirred 3 h at room temperature. The mixture was poured into 1M pH7 phosphate buffer and the organic phase extracted twice with ethyl acetate. The combined organic phases were washed with brine, dried over sodium sulfate and evaporated to dryness. The oily residue was purified by column chromatography on silica gel (6:1 to 5:1 hexane/ethyl acetate eluant) to afford the product as an oil (29 g, 67% over two steps) which solidified upon standing in the refrigerator. m.p. 55–56° C. 6-Ethoxy-2,3-dihydro-1H-3a-aza-cyclopenta[a]indene [2-(5-Chloro-pent-1-ynyl)-4-ethoxy-phenyl]-carbamic acid methyl ester (28.5 g, 96.36 mmol) was dissolved in acetonitrile (600 mL). Palladium (II) chloride (0.9 g, 5.08 mmol) was added and the mixture was heated 2 h at 70° C. The dark mixture was cooled to room temperature and filtered through a small pad of celite, while washing the pad with acetonitrile. The solvent was evaporated to dryness and the brown residue (30 g) taken up in tert-butanol (600 mL). Powdered potassium hydroxide (22 g, 392.09 mmol) was added and the mixture stirred 40 min in an oil-bath at 105° C. The mixture was cooled, poured onto ice and extracted twice with ethyl acetate. The combined organic phases were washed with water, brine, dried over sodium sulfate and evaporated. The brown residue was purified by column chromatography on silica gel (5:1 hexane/ethyl acetate) to afford the product as an off-white solid (13.4 g, 69%). m.p.101–102° C.

Route B Synthesis from 4-bromoaniline a) 4-Bromo-phenyl)-carbamic acid methyl ester 1000 mL of a 10% aqueous sodium bicarbonate solution was added to a solution of 100 g (0.5813 mol) p-bromoaniline in 1000 mL dichloromethane. The mixture was cooled to 0° C. and 66.3 g (54 mL, 0.702 mol) methyl chloroformate were added with stirring over 15 min. The resulting mixture was stirred at room temperature for 4 h. The phases were separated, the organic phase was washed with brine, dried with magnesium sulfate and filtered. The mother liquor was diluted with 1500 mL n-hexane and concentrated to ca. 1000 mL, whereby a precipitate formed. The product was collected by filtration and dried to yield 133.2 g (99%) of the title compound as white crystals melting at 125.6–126.5° C.

b) (4-Bromo-2-iodo-phenyl)-carbamic acid methyl ester 133 g (0.591 mol) N-iodosuccinimide and 5.0 mL (8.60 g, 0.0573 mol) trifluoromethanesulfonic acid were added to a solution of 130.0 g (0.5651 mol) of (4-bromo-phenyl)-carbamic acid methyl ester in 660 mL acetonitrile. The mixture was stirred at room temperature for 18 h. The precipitate was collected by filtration washed with 160 mL ice-cold acetonitrile and dried to constant weight to yield 187.0 g (92%) of the title compound as white crystals melting at 129.4–130.0° C.

c) 6-Bromo-2,3-dihydro-1H-3a-aza-cyclopenta[a]indene

A suspension of 3.350 g (0.0048 mol) bis-(triphenylphosphine)-palladium(II)dichloride and 1.90 g (0.010 mol) copper(I)iodide in 500 mL triethylamine was heated to reflux for 30 min. The mixture was cooled to room temperature and 190 g (0.534 mol) (4-bromo-2-iodo-phenyl)-carbamic acid methyl ester and 66.462 mL 5-chloro-1-pentyne (65 g, 0.634 mol) were added. The mixture was heated to reflux. When a temperature of 70° C. was reached, a strong exothermic reaction was observed leading to vigorous reflux! A thick suspension formed. Refluxing was continued for 15 min. The mixture was cooled to room temperature and diluted with 500 mL ethyl acetate. The solids were removed by filtration and the filter cake was washed with ca. 200 mL ethyl acetate. The filtrate was concentrated under aspirator vacuum, taken up in 500 mL ethyl acetate and washed successively with 10% citric acid solution, 10% sodium thiosulfate solution, 10% sodium bicarbonate solution and brine. The aqueous phases were re-extracted with ethyl acetate. The combined organic phases were dried over magnesium sulfate. To the solution was added 200 mL dimethylsulfoxide and the mixture concentrated under aspirator vacuum. Remaining ethyl acetate was removed under high vacuum. The resulting dimethylsulfoxide solution was added to a suspension of 70 g lithium hydroxide monohydrate in 120 mL water and 1000 mL dimethylsulfoxide. The resulting suspension was heated to 80° C. for 2 h. The mixture was cooled to room temperature and 1500 mL of ice water and 600 mL dichloromethane were added. The pH was adjusted to 6 by addition of 25% hydrochloric acid. The phases were separated and the organic phase was washed with half concentrated brine. The aqueous phases were extracted with 200 mL dichloromethane. The combined organic phases were diluted to a volume of 2000 mL with n-hexane. The resulting solution was filtered over 1 kg silica gel with hexane:dichloromethane=2: 1. The product fractions were combined and concentrated under aspirator vacuum, whereby crystallisation occurred to yield 95 g white crystals. (HPLC 100%). The mother liquor was evaporated to afford a second crop [7.2 g, 87% purity by HPLC) which was recrystallised to furnish a further 6 g (100% purity by HPLC) Total yield: 101 g (80%) of the title compound as white crystals, m.p.: 78.7–79.4° C.

d) 2,3-Dihydro-1H-3a-aza-cyclopenta[a]inden-6-ol 187.5 mL of a 1.6M solution of n-butyllithium (0.30 mol) in n-hexane was added over 20 min to a cooled (–78° C.) solution of 47.2 g 6-bromo-2,3-dihydro-1H-3a-aza-cyclopenta[a]indene (0.20 mol) in 800 mL tetrahydrofuran. The resulting beige suspension was warmed to –50° C. and stirred at this temperature for 45 min. The mixture was cooled to –78° C., and 92.0 mL (0.40 mol) triisoproyl-borate was added over 10 min. The mixture was stirred 30 min at –78° C. and allowed to warm to 0° C. over 30 min. The slightly turbid mixture was stirred at 0–10° C. for 15 min and 100 mL (0.875 mol) 50% acetic acid were added dropwise. To the resulting solution were added over 15 min 30 mL of a 35% hydrogen peroxide solution (0.31 mol) at a temperature of 0–5° C. The mixture was stirred at 0° C. for 30 min and at room temperature for 1 h. The reaction mixture was diluted with 2500 mL diethyl ether and 1000 mL water. The phases were separated and the organic phase was washed with 1000 mL water, twice with 1000 mL 5% sodium thiosulfate, again with 1000 mL water and finally with 1000 mL brine, dried over sodium sulfate and concentrated under aspirator vacuum. The solid residue was stirred with 500 mL n-hexane for 1 h. The product was collected by filtration and dried to constant weight under aspirator vacuum at room temperature to yield 32.56 g (94%) of the title compound as beige crystals melting at 116–118° C.

e) 6-Ethoxy-2,3-dihydro-1H-3a-aza-cyclopenta[a]indene a solution of 64.00 g 2,3-dihydro-1H-3a-aza-cyclopenta[a]inden-6-ol in 240 mL N,N-dimethylformamide was added over 10 min to a cooled (0° C.) suspension of 17.73 g (0.406 mol) sodium hydride (55% in oil) in 400 mL N,N-dimethylformamide. The mixture was stirred at 0° C. for 30 min. To the resulting mixture was added 32.84 mL (63.39 g, 0.406mol) ethyl iodide dropwise over 10 min. The mixture was stirred at room temperature for 1 h. The mixture was partitioned between ice-water and ethyl acetate. The phases were separated and the organic phase was washed with 10% citric acid, 10% sodium bicarbonate solution and brine. The aqueous phases were re-extracted with ethyl acetate. The combined organic phases were dried over magnesium sulfate and evaporated to dryness. The solid residue was stirred with 600 mL n-hexane for 1 h and the product collected by filtration. The filtrate was concentrated to obtain a second crop of product, to afford a combined yield of 66.4 g (89.3%) of the title compound as white crystals melting at 101–102° C.

f) 6-Ethoxy-8-iodo-2,3-dihydro-1H-3a-aza-cyclopenta[a]indene

A solution of 51.64 g (0.230 mol) N-iodosuccimimide in 330 mL acetonitrile over 15 min was added at 30° C. (before any starting material precipitated)to a solution of 44.00 g (0.201 mol) 6-ethoxy-2,3-dihydro-1H-3a-aza-cyclopenta[a]indene in 440 mL acetonitrile (slight warming was necessary. The reaction mixture was immediately cooled to 0° C. and stirred at this temperature for 30 min. The raw product was collected by filtration and re-crystallized from 500 mL acetonitrile to yield 56.2 g (78.6%) of the title compound. The mother liquor was concentrated and the residue was recrystallised from 25 mL acetonitrile to yield another 2.00 g (2.7%) of the title compound. Total yield: 58.2 g (81.4%). m.p.: 128–129° C.;.

g) [2-(6-Ethoxy-2,3-dihydro-1H-3a-aza-cyclopenta[a]inden-8-yl)-1-methyl-ethyl]-carbamic acid tert-butyl ester 75 mL of a pre-cooled (−78° C.) 1.6M solution of n-butyllithium in n-hexane at −78° C. was added over 30 min to a suspension of 32.72 g (0.100 mol) 6-ethoxy-8-iodo-2,3-dihydro-1H-3a-aza-cyclopenta[a]indene in 330 mL dry tetrahydrofuran. The mixture was stirred 5 min at −78° C. and 30.85 g (S)-4-methyl-2,2-dioxo-[1,2,3]oxathiazolidine-3-carboxylic acid tert-butyl ester was added in one portion. The mixture was stirred 20 min at −78° C. The reaction mixture was allowed to warm to −30° C. over 50 min. To the resulting slightly turbid mixture was added 300 mL of 10% citric acid. The phases were separated and the aqueous phase was extracted with 200 mL hexane. The combined organic phases were washed with 200 mL brine, dried over magnesium sulfate and evaporated. The residue was taken up in 200 mL dichloromethane and purified by chromatography on 1500 g silica gel (43–60 mesh) with dichloromethane (4000 mL) and 19:1 dichloromethane/ethyl acetate (6000 mL). The product fractions were evaporated and the residue was dissolved in 200 mL dichloromethane. The solution was diluted with 1000 mL hexane and the mixture was concentrated to a volume of 800 mL. The resulting suspension was stirred 18 h at room temperature. The mixture was cooled to 0° C. and stirred 30 min. The product was collected by filtration to yield 22.00 g of the title compound. The mother liquor was purified by chromatography, resulting in a further 4.71 g of the title compound. Total yield: 26.71 g (74.5%). m.p.: 89–90° C.

h) (S)-2-(6-Ethoxy-2,3-dihydro-1H-3a-aza-cyclopenta[a]inden-8-yl)-1-methyl-ethylamine; hydrochloride A solution of 80.00 g (0.223 mol) [2-(6-ethoxy-2,3-dihydro-1H-3a-aza-cyclopenta[a]inden-8-yl)-1-methyl-ethyl]-carbamic acid tert-butyl ester in a 2.26M solution of hydrochloric acid in ethyl acetate was stirred at room temperature for 1 h. The resulting suspension was diluted with 200 mL ethyl acetate and the product collected by filtration to yield 59.60 g (90.6%) of the title compound as an off-white solid. (The mother liquor was concentrated to yield another 6.6 g as a slightly pink solid). Total yield: 66.2 g (100%). mp.: 225° C. (dec).

Example 2

Preparation of (S)-2-[6-(2-methoxy-ethoxy)-2,3-dihydro-1H-3a-aza-cyclopenta[a]inden-8-yl]-1-methyl-ethyl amine:

a) 6-[Dimethyl-(1,1,2-trimethyl-propyl)-silanyloxy]-8-iodo-2,3-dihydro-1H-3a-aza-cyclopenta[a]indene 8.8 g imidazole and 21.25 g thexylchloride was added at room temperature to a solution of 17.16 g 2,3-dihydro-1H-3a-aza-cyclopenta[a]inden-6-ol in 80 mL N,N-dimethylformamide and the mixture is stirred at ambient temperature over night. The reaction mixture was distributed between water and ethyl acetate and the phases were separated. The organic phase was washed with water 10% citric acid, 10% sodium bicarbonate and brine, dried over magnesium sulfate and evaporated to dryness. The residue was purified by chromatography on silica gel with dichloromethane: hexane=1:1 to yield 25.58 g of a solidifying colourless oil. To a solution of 25.0 g of this material in 100 mL acetonitrile was added at −10° C. (acetone-ice bath) 17.82 g N-iodosuccinimide at once with efficient stirring. A new precipitate formed rapidly. Stirring at −10° C. continued for 30 min. The mixture was diluted with ca 70 mL cold acetonitrile to obtain a filterable suspension. The product was collected by filtration and washed with ca 70 mL ice-cold acetonitrile and dried to constant weight under high vacuum at 40° C. to yield 30.0 g 6-[dimethyl-(1,1,2-trimethyl-propyl)-silanyloxy]-8-iodo-2,3-dihydro-1H-3a-aza-cyclopenta[a]indene as beige crystals melting at 97–98° C.

b) (S)-[2-(6-Hydroxy-2,3-dihydro-1H-3a-aza-cyclopenta[a]inden-8-yl)-1-methyl-ethyl]-carbamic acid tert-butyl ester 51.3 mL of a 1.6M solution of n-butyllithium in n-hexane was added dropwise with stirring at −78° C. to a suspension of 30.00 g 6-[dimethyl-(1,1,2-trimethyl-propyl)-silanyloxy]-8-iodo-2,3-dihydro-1H-3a-aza-cyclopenta[a]indene in 200 mL tetrahydrofuran. The mixture was stirred at −78° C. for 30 min. To the resulting suspension 19.35 g (S)- -methyl-2,2-dioxo-[1,2,3]oxathiazolidine-3-carboxylic acid tert-butyl ester was added, the mixture was stirred at −78° C. for 30 min and then allowed to warm to room temperature during ca 2 h. The reaction mixture was distributed between ice-cold 10% citric acid and ethyl acetate. The phases separated, the organic phase washed with water and brine, dried over magnesium sulfate and evaporated.

The residue was purified by chromatography on silica gel with hexane: ethyl acetate=9: 1 to yield 27.53 g of a white solid which is dissolved in 250 mL methanol. 10 g ammonium fluoride was added to the resulting solution and the mixture stirred for 18 h at room temperature. The reaction mixture was distributed between water and ethyl acetate. The phases separated, the organic phase was washed with water 10% citric acid, 10% sodium bicarbonate and brine, dried over magnesium sulfate and evaporated. The residue was taken up in hexane whereby crystallisation took place. The solid was collected by filtration and dried to constant weight to yield 17.00 g of (S)-[2-(6-hydroxy-2,3-dihydro-1H-3a-aza-cyclopenta[a]inden-8-yl)-1-methyl-ethyl]-carbamic acid tert-butyl ester melting at 135–136° C.

c) (S)-2-[6-(2-Methoxy-ethoxy)-2,3-dihydro-1H-3a-aza-cyclopenta[a]inden-8-yl]-1-methyl-ethylamine hydrochloride 0.044 g sodium hydride 55–65% in oil was added to a solution of 0.33 g (S)-[2-(6-hydroxy-2,3-dihydro-1H-3a-aza-cyclopenta[a]inden-8-yl)-1-methyl-ethyl]-carbamic acid tert-butyl ester in 3 mL N,N-dimethylformamide. The mixture was stirred at room temperature for 30 min. To the resulting mixture 0.167 g 2-bromoethyl methyl ether was added and the reaction mixture stirred at room temperature for 18 h. The reaction mixture was distributed between water and ethyl acetate. The phases separated and the organic phase was washed with water, 10% citric acid, 10% sodium bicarbonate and brine, dried over magnesium sulfate and evaporated. The residue was purified by chromatography on silica gel with hexane:ethyl acetate=3:1. The product fractions were evaporated and the residue taken up in 3.3 mL of a 2.26 M solution of hydrochloric acid in ethyl acetate. The mixture was stirred at room temperature for 18 h. The solid was collected by filtration washed with ethyl acetate and dried to constant weight to yield 0.26 g (S)-2-[6-(2-methoxy-ethoxy)-2,3-dihydro-1H-3a-aza-cyclopenta[a]inden-8-yl]-1-methyl-ethylamine hydrochloride as white crystals melting at 194.6–195.3° C.

Example 3

Preparation of (S)-2-(6-cyclopropoxy-2,3-dihydro-1H-3a-aza-cyclopenta[a]inden-8-yl)-1-methyl-ethylamine:

a) 6-Cyclopropoxy-2,3-dihydro-1H-3a-aza-cyclopenta[a]indene 6.00 g sodium hydride 55–65% in oil in portion was added during ca 30 min at room temperature to a solution of 23.5 g 2,3-dihydro-1H-3a-aza-cyclopenta[a]inden-6-ol in 200 mL dimethylsulfoxide. 18.75 g potassium carbonate and 1.700 g potassium iodide and 34 mL cyclopropylbromide was added to the resulting solution. The resulting suspension was stirred under argon at 100° C. for 48 h. Another 17 mL cyclopropylbromide was added. The resulting suspension was stirred under argon at 100° C. for 24 h. The reaction mixture was diluted with water and extracted with dichloromethane. The organic phase was purified by chromatography on silica gel with hexane:dichloromethane=1:1 to yield 17.75 g 6-Cyclopropoxy-2,3-dihydro-1H-3a-aza-cyclopenta[a]indene as a white crystalline solid melting at 61–63° C.

b) 6-Cyclopropoxy-8-iodo-2,3-dihydro-1H-3a-aza-cyclopenta[a]indene 18.5 g N-iodosuccinimide at 0° C. was added to a solution of 17.55 g 6-cyclopropoxy-2,3-dihydro-1H-3a-aza-cyclopenta[a]indene in acetonitrile and the mixture was stirred at this temperature for 15 min. The solid was collected by filtration, washed with cold acetonitrile and dried to constant weight to yield 20.1 g 6-cyclopropoxy-8-iodo-2,3-dihydro-1H-3a-aza-cyclopenta[a]indene as beige crystals melting at 104–105° C.

c) (S)-[2-(6-Cyclopropoxy-2,3-dihydro-1H-3a-aza-cyclopenta[a]inden-8-yl)-1-methyl-ethyl]-carbamic acid tert-butyl ester 37.4 mL of a 1.6 M solution of n-butyllithium in n-hexane was added at −78° C. dropwise during 10 min to a solution of 18.65 g 6-cyclopropoxy-8-iodo-2,3-dihydro-1H-3a-aza-cyclopenta[a]indene in 250 mL tetrahydrofuran. The mixture was stirred at −78° C. for 30 min. 15.55 g (S)-4-methyl-2,2-dioxo-[1,2,3]oxathiazolidine-3-carboxylic acid tert-butyl ester was added to the resulting suspension and the mixture stirred at −78° C. for 30 min and at 0° C. for 45 min. The reaction mixture was distributed between ice-cold 10% citric acid and ethyl acetate. The phases separated, the organic phase washed with water and brine, dried over magnesium sulfate and evaporated. The residue was purified by chromatography on silica gel with hexane: ethyl acetate= 4: 1 to yield 11.91 g (S)-[2-(6-cyclopropoxy-2,3-dihydro-1H-3a-aza-cyclopenta[a]inden-8-yl)-1-methyl-ethyl]-carbamic acid tert-butyl ester as beige crystals melting at 83–84° C.

d) (S)-2-(6-cyclopropoxy-2,3-dihydro-1H-3 a-aza-cyclopenta[a]inden-8-yl)-1-methyl-ethylamine; hydrochloride A solution of 11.81 g (S)-[2-(6-cyclopropoxy-2,3-dihydro-1H-3a-aza-cyclopenta[a]inden-8-yl)-1-methyl-ethyl]-carbamic acid tert-butyl ester in 120 mL of a 2.26 M solution of hydrochloric acid in ethyl acetate was stirred at room temperature for 2 h. The resulting suspension was diluted with 120 mL ethyl acetate and the product collected by filtration, washed with ethyl acetate and dried to constant weight under high vacuum to yield 8.65 g (S)-2-(6-cyclopropoxy-2,3-dihydro-1H-3a-aza-cyclopenta[a]inden-8-yl)-1-methyl-ethylamine hydrochloride as white crystals melting at 214–217° C.

Example 4

Preparation of (S)-2-[8-(2-amino-propyl)-2,3-dihydro-1H-3a-aza-cyclopenta[a]inden-6-yloxy]-ethanol:

a) (S)-[8-(2-tert-Butoxycarbonylamino-propyl)-2,3-dihydro-1H-3a-aza-cyclopenta[a]inden-6-yloxy]-acetic acid methyl ester 0.42 g sodium hydride 55–65% in oil was added to a solution of 3.3 g (S)-[2-(6-hydroxy-2,3-dihydro-1H-3a-aza-cyclopenta[a]inden-8-yl)-1-methyl-ethyl]-carbamic acid tert-butyl ester in 30 mL dimethylsulfoxide and the mixture stirred at room temperature for 30 min. 1.68 g bromoacetic acid methyl ester was added to the resulting solution and the mixture stirred at room temperature for 2 h. The mixture was distributed between water and ethyl acetate. The phases separated and the organic phase was washed with water and brine, dried over magnesium sulfate and evaporated to dryness. The residue crystallised under hexane and was dried to constant weight to yield 3.61 g of (S)-[8-(2-tert-butoxycarbonylamino-propyl)-2,3-dihydro-1H-3a-aza-cyclopenta[a]inden-6-yloxy]-acetic acid methyl ester as off white crystals melting at 87–88° C.

b) (S)-2-[8-(2-Amino-propyl)-2,3-dihydro-1H-3a-aza-cyclopenta[a]inden-6-yloxy]-ethanol hydrochloride 0.022 g lithium borohydride was added to a solution of 0.40 g (S)-[8-(2-tert-butoxycarbonylamino-propyl)-2,3-dihydro-1H-3a-aza-cyclopenta[a]inden-6-yloxy]-acetic acid methyl ester in 4 mL tetrahydrofuran and the mixture stirred at room temperature for 2 h. The reaction mixture was distributed between water and ethyl acetate. The phases separated, the organic phase was washed with water and brine, dried over magnesium sulfate and evaporated. The residue was purified by chromatography on silica gel. The product fractions were evaporated and the residue taken up in 3 mL of a 2 M solution of hydrochloric acid in dioxane. The mixture was stirred at room temperature for 18 h. The solid was collected by filtration, washed with dioxane and dried to constant weight to yield 0.22 g (S)-2-[8-(2-aminopropyl)-2,3-dihydro-1H-3a-aza-cyclopenta[a]inden-6-yloxy]-ethanol hydrochloride as white crystals. MS: M+H= 275.3 M+H−NH3=258.1

Intermediate F (S)-4-Methyl-2,2-dioxo-[1,2,3]oxathiazolidine-3-carboxylic acid tert-butyl ester 120 ml of a ca 1.6 M solution of n-butyllithium in n-hexane was added with stirring during 15 min. to a solution of 17.5 g (S)-N-BOC-alaninol in 120 ml tetrahydrofuran at −78° C. The mixture was then stirred at −15° C. for 45 min. The mixture was then cooled to −78° C. and a solution of 7.3 mL thionyl chloride in 50 mL THF, cooled to −78° C. in a jacketed dropping funnel, was added at once with vigorous stirring. The temperature rose to ca −38° C. The mixture was then stirred at −15° C. for 1 h. The reaction mixture was distributed between 10% citric acid and ethyl acetate. The phases separated, the organic phase was washed with 10% sodium bicarbonate and brine, dried over magnesium sulfate and evaporated. The residue was taken up in 150 mL ethyl acetate and a solution of 35 g sodium metaperiodate was added at 0° C. 0.20 g ruthenium dioxide hydrate was added to the well stirred mixture. The mixture was stirred at room temperature for 1.5 h. The phases were separated. The organic phase was purified by chromatography on silica gel with ethyl acetate: hexane=2: 1 to yield 13.79 g (S)-4-Methyl-2,2-dioxo-[1,2,3]oxathiazolidine-3-carboxylic acid tert-butyl ester as white crystals melting at 121.1–121.8° C. after recrystallisation from t-butylmethylether.

Example 5

Preparation of (S)-2-[6-(3-methoxy-propoxy)-2,3-dihydro-1H-3a-aza-cyclopenta[a]inden-8-yl]-1-methyl-ethylamine:

0.937 g sodium hydride 55–65% in oil was added to a solution of 6.45 g (S)-[2-(6-hydroxy-2,3-dihydro-1H-3a-aza-cyclopenta[a]inden-8-yl)-1-methyl-ethyl]-carbamic acid tert-butyl ester in 75 mL N,N-dimethylformamide. The mixture was stirred at room temperature for 30 min. 5.72 g toluene-4-sulfonic acid 3-methoxy-propyl ester in 15 mL N,N-dimethylformamide was added to the resulting mixture and the reaction mixture was stirred at room temperature for 18 h. The reaction mixture was distributed between water and ethyl acetate. The phases separated, and the organic phase was washed with water, 10% citric acid, 10% sodium bicarbonate and brine, dried over magnesium sulfate and evaporated. The residue was purified by chromatography on silica gel with hexane:ethyl acetate=4:1. The product fractions were evaporated and the residue taken up in 86mL of a 2.16 M solution of hydrochloric acid in ethyl acetate. The mixture was stirred at room temperature for 18 h. The solid was collected by filtration, washed with ethyl acetate and dried to constant weight to yield 5.95 g (S)-2-[6-(3-methoxy-propoxy)-2,3-dihydro-1H-3a-aza-cyclopenta[a]inden-8-yl]-1-methyl-ethylamine hydrochloride as white crystals melting at 188–190° C.

Example 6

Preparation of (S)-2-[6-(4-methoxy-butoxy)-2,3-dihydro-1H-3a-aza-cyclopenta[a]inden-8-yl]-1-methyl-ethylamine hydrochloride:

35 mg sodium hydride 55–65% in oil was added to a solution of 244 mg (S)-[2-(6-hydroxy-2,3-dihydro-1H-3a-aza-cyclopenta[a]inden-8-yl)-1-methyl-ethyl]-carbamic acid tert-butyl ester in 4 mL N,N-dimethylformamide. The mixture was stirred at room temperature for 30 min. 229 mg toluene-4-sulfonic acid 4-methoxy-butyl ester was added to the resulting mixture and the reaction mixture stirred at room temperature for 7 h. The reaction mixture was distributed between water and ethyl acetate. The phases separated and the organic phase was washed with water, 10% citric acid, 10% sodium bicarbonate and brine, dried over magnesium sulfate and evaporated. The residue was purified by chromatography on silica gel with hexane:ethyl acetate=4:1. The product fractions were evaporated and the residue taken up in 6 mL of a 2.16 M solution of hydrochloric acid in ethyl acetate. The mixture was stirred at room temperature for 7 h. The solid collected by filtration was washed with ethyl acetate and dried under vacuum to yield 148 mg (S)-2-[6-(4-methoxy-butoxy)-2,3-dihydro-1H-3a-aza-cyclopenta[a]inden-8-yl]-1-methyl-ethylamine hydrochloride as white crystals melting at 107° C.

Example 7

Preparation of (S)-2-[6-(2-ethoxy-ethoxy)-2,3-dihydro-1H-3a-aza-cyclopenta[a]inden-8-yl]-1-methyl-ethylamine hydrochloride:

44 mg sodium hydride 55–65% in oil was added to a solution of 333 mg (S)-[2-(6-hydroxy-2,3-dihydro-1H-3a-aza-cyclopenta[a]inden-8-yl)-1-methyl-ethyl]-carbamic acid tert-butyl ester in 3 mL N,N-dimethylformamide. The mixture was stirred at room temperature for 30 min. 204 mg 2-bromoethoxy ethyl ether was added to the resulting mixture and the reaction mixture was stirred at room temperature for 2 h. The reaction mixture was distributed between water and ethyl acetate. The phases separated and the organic phase was washed with water, 10% citric acid, 10% sodium bicarbonate and brine, dried over magnesium sulfate and evaporated. The residue was purified by chromatography on silica gel with hexane:ethyl acetate=4:1. The product fractions were evaporated and the residue taken up in 3 mL of a 2.16 M solution of hydrochloric acid in ethyl acetate. The mixture was stirred at room temperature for 7 h. The solid was collected by filtration, washed with ethyl acetate and dried under vacuum to yield 244 mg (S)-2-[6-(2-ethoxy-ethoxy)-2,3-dihydro-1H-3a-aza-cyclopenta[a]inden-8-yl]-1-methyl-ethylamine hydrochloride as white crystals melting at 170–172° C.

Example 8

Preparation of (S)-2-[6-(3-ethoxy-propoxy)-2,3-dihydro-1H-3a-aza-cyclopenta[a]inden-8-yl]-1-methyl-ethylamine hydrochloride:

44 mg sodium hydride 55–65% in oil was added to a solution of 330 mg (S)-[2-(6-hydroxy-2,3-dihydro-1H-3a-aza-cyclopenta[a]inden-8-yl)-1-methyl-ethyl]-carbamic acid tert-butyl ester in 5 mL N,N-dimethylformamide. The mixture was stirred at room temperature for 30 min. 310 mg toluene-4-sulfonic acid 3-ethoxy-propyl ester was added to the resulting mixture and the reaction mixture stirred at room temperature for 6 h. The reaction mixture was distributed between water and ethyl acetate, the phases separated, and the organic phase was washed with water, 10% citric acid, 10% sodium bicarbonate and brine, dried over magnesium sulfate and evaporated. The residue was purified by chromatography on silica gel with hexane:ethyl acetate=4:1. The product fractions were evaporated and the residue was taken up in 5 mL of a 2.16 M solution of hydrochloric acid in ethyl acetate. The mixture was stirred at room temperature for 5 h. The solid was collected by filtration, washed with ethyl acetate and dried under vacuum to yield 255 mg (S)-2-[6-(3-ethoxy-propoxy)-2,3-dihydro-1H-3a-aza-cyclopenta[a]inden-8-yl]-1-methyl-ethylamine hydrochloride as white crystals melting at 132° C.

Example 9

Preparation of (S)-2-{6-[2-(2-methoxy-ethoxy)-ethoxy]-2,3-dihydro-1H-3a-aza-cyclopenta[a]inden-8-yl}-1-methyl-ethyl amine 25 mg sodium hydride 55–65% in oil was added to a solution of 165 mg (S)-[2-(6-hydroxy-2,3-dihydro-1H-3a-aza-cyclopenta[a]inden-8-yl)-1-methyl-ethyl]-carbamic acid tert-butyl ester in 1.5 mL N,N-dimethylformamide. The mixture was stirred at room temperature for 30 min, then 122 mg 1-bromo-2-(2-methoxyethoxy)-ethane was added to the mixture and the mixture was stirred at room temperature for an additional 7 h. The reaction mixture was distributed between water and ethyl acetate. The phases were separated, the organic phase is washed with water, 10% citric acid, 10% sodium bicarbonate and brine, dried over magnesium sulfate and evaporated. The residue was purified by chromatography on silica gel with hexane:ethyl acetate=4:1. The product fractions were evaporated and the residue taken up in 1.5 mL of a 2.16 M solution of hydrochloric acid in ethyl acetate. The mixture was stirred at room temperature for 3 h. The solid was collected by filtration, neutralised with aqueous ammonium hydroxide and purified by chromatography on silica gel with dichloromethane:methanol:aqueous ammonium hydroxide=90:9:1. The product fractions are dried over magnesium sulfate and evaporated to yield 82 mg (S)-2-{6-[2-(2-methoxy-ethoxy)-ethoxy]-2,3-dihydro-1H-3a-aza-cyclopenta[a]inden-8-yl}-1-methyl-ethylamine as light brown oil. MS: M+H=333.3; M+H–NH3=316.3.

Example 10

Preparation of (S)-2-{6-[3-(2-methoxy-ethoxy)-propoxy]-2,3-dihydro-1H-3a-aza-cyclopenta[a]inden-8-yl}-1-methyl-ethylamine 25 mg sodium hydride 55–65% in oil was added to a solution of 165 mg (S)-[2-(6-hydroxy-2,3-dihydro-1H-3a-aza-cyclopenta[a]inden-8-yl)-1-methyl-ethyl]-carbamic acid tert-butyl ester in 1.5 mL N,N-dimethylformamide. The mixture was stirred at room temperature for 30 min, then 120 mg 3-(methoxyethoxy)propyl bromide was added added and the reaction mixture was stirred at room temperature for an additional 22 h. The reaction mixture was distributed between water and ethyl acetate. The phases were separated, the organic phase washed with water, 10% citric acid, 10% sodium bicarbonate and brine, dried over magnesium sulfate and evaporated. The residue was purified by chromatography on silica gel with hexane:ethyl acetate=4:1. The product fractions were evaporated and the residue taken up in 4.0 mL of a 2.16 M solution of hydrochloric acid in ethyl acetate. The mixture was stirred at room temperature for 1 h, the solid collected by filtration, neutralised with aqueous ammonium hydroxide and purified by chromatography on silica gel with dichloromethane:methanol:aqueous ammonium hydroxide=90:9:1. The product fractions were dried over magnesium sulfate and evaporated to yield 80 mg (S)-2-{6-[3-(2-methoxy-ethoxy)-propoxy]-2,3-dihydro-1H-3a-aza-cyclopenta[a]inden-8-yl}-1-methyl-ethylamine as light brown oil. MS: M+H=347.5; M+H–NH3=330.4.

Example 11

Preparation of (S)-2-(6-Ethoxy-5-fluoro-2,3-dihydro-1H-3a-aza-cyclopenta[a]inden-8-yl)-1-methyl-ethylamine a) The starting material (4-bromo-3-fluoro-phenyl)-carbamic acid methyl ester was prepared by the following procedure 19.6 g N-bromosuccinimide and 1.5 g (0.88 ml) trifluoromethansulfonic acid was added to a solution of 16.92 g (3-fluoro-phenyl)-carbamic acid methyl ester in 200 ml acetonitrile and the mixture was stirred at room temperature for 3 h. The reaction mixture was partitioned between water and ethyl acetate, the phases were separated and the organic phase was washed with saturated sodium bicarbonate and brine and purified by chromatography on silicagel with hexane: ethyl acetate=4:1 to yield 18.7 g (75% Th) of the title compound as a white crystalline solid. M.p.: 121–122° C.

Following the same general procedure as in example 1 path B the following intermediates were prepared.

b) (4-Bromo-5-fluoro-2-iodo-phenyl)-carbamic acid methyl ester m.p.:99–100° C.
  c) 6-Bromo-5-fluoro-2,3-dihydro-1H-3a-aza-cyclopenta[a]indene m.p.: 108–109° C.
  d) 5-Fluoro-2,3-dihydro-1H-3a-aza-cyclopenta[a]inden-6-ol m.p.:128° C.

Following the same general procedure as in example 2 the following intermediates were prepared e) 6-[Dimethyl-(1,1,2-trimethyl-propyl)-silanyloxy]-5-fluoro-2,3-dihydro-1H-3a-aza-cyclopenta[a]indene m.p.:55–58° C.
  f) 6-[Dimethyl-(1,1,2-trimethyl-propyl)-silanyloxy]-5-fluoro-8-iodo-2,3-dihydro-1H-3a-aza-cyclopenta[a]indene m.p.:94–97° C.
  g) (S)-[2-(5-Fluoro-6-hydroxy-2,3-dihydro-1H-3a-aza-cyclopenta[a]inden-8-yl)-1-methyl-ethyl]-carbamic acid tert-butyl ester MS: M+H=349.4 and M+Na=371 m.p.: 141–143° C.
  h) The title compound was obtained in an analogy to the preparation of example 2 by alkylating the above intermediate (S)-[2-(5-Fluoro-6-hydroxy-2,3-dihydro-1H-3a-aza-cyclopenta[a]inden-8-yl)-1-methyl-ethyl]-carbamic acid tert-butyl ester with ethyl iodide and removal of the BOC protection group. The compound was isolated as the free base and melted at 107° C.

Example 12

(S)-2-[5-Fluoro-6-(2-methoxy-ethoxy)-2,3-dihydro-1H-3a-aza-cyclopenta[a]inden-8-yl]-1-methyl-ethylamine hydrochloride By the same general procedure as in example 2 the title compound was obtained from (S)-[2-(5-Fluoro-6-hydroxy-2,3-dihydro-1H-3a-aza-cyclopenta[a]inden-8-yl)-1-methyl-ethyl]-carbamic acid tert-butyl ester as white crystals m.p.: 198–199° C.

Example 13

(S)-2-[5-Fluoro-6-(3-methoxy-propoxy)-2,3-dihydro-1H-3a-aza-cyclopenta[a]inden-8-yl]-1-methyl-ethylamine hydrochloride By the same general procedure as in example 5 the title compound was obtained from (S)-[2-(5-Fluoro-6-hydroxy- 2,3-dihydro-1H-3a-aza-cyclopenta[a]inden-8-yl)-1-methyl-ethyl]-carbamic acid tert-butyl ester as white crystals. m.p.:212–214° C.

Example 14

(S)-2-[8-(2-Amino-propyl)-5-fluoro-2,3-dihydro-1H-3a-aza-cyclopenta[a]inden-6-yloxy]-ethanol hydrochloride By the same general procedure as in example 4 the title compound was obtained from (S))-[2-(5-Fluoro-6-hydroxy-2,3-dihydro-1H-3a-aza-cyclopenta[a]inden-8-yl)-1-methyl-ethyl]-carbamic acid tert-butyl ester as white crystals. m.p.:142–144° C.

Example 15

Preparation of (S)-2-(6-Ethoxy-7-fluoro-2,3-dihydro-1H-3a-aza-cyclopenta[a]inden-8-yl)-1-methyl-ethylamine hydrochloride a) The starting material (3-fluoro-2-iodo-phenyl)-carbamic acid methyl ester was prepared from (3-fluoro-phenyl)-carbamic acid methyl ester by double deprotonation with sec.butyllithium in tetrahydrofuran at −78° C. followed by reaction with iodine. m.p.:80–82° C.

b) (4-Bromo-3-fluoro-2-iodo-phenyl)-carbamic acid methyl ester was prepared from (3-fluoro-2-iodo-phenyl)-carbamic acid methyl ester by reaction with N-bromosuccinimide in acetonitrile in the presence of trifluoromethansulfonic acidm.p.:162–164° C.

c) 6-Bromo-7-fluoro-2,3-dihydro-1H-3a-aza-cyclopenta[a]indene was obtained by the same general procedure as in example 1 path B from the above intermediate. m.p.:78–80 MS: M=253.0, 255.0 d) Following the same general procedure as in example 1 and 2 the following intermediates were prepared e) 7-Fluoro-2,3-dihydro-1H-3a-aza-cyclopenta[a]inden-6-ol f) 6-[Dimethyl-(1,1,2-trimethyl-propyl)-silanyloxy]-7-fluoro-2,3-dihydro-1H-3a-aza-cyclopenta[a]indene g) 6-[Dimethyl-(1,1,2-trimethyl-propyl)-silanyloxy]-5-fluoro-8-iodo-2,3-dihydro-1H-3a-aza-cyclopenta[a]indene h) Following the same general procedures as in example 11 (S)-[2-(7-Fluoro-6-hydroxy-2,3-dihydro-1H-3a-aza-cyclopenta[a]inden-8-yl)-1-methyl-ethyl]-carbamic acid tert-butyl ester was obtained.

The product of example 15 was obtained from the above intermediate by reaction with ethyliodide in dimethylformamide in the presence of sodium hydride and cleavage of the tert.butyloxycarbonyl protective group with hydrochloric acid in ethyl acetate.

Example 16

Preparation of (S)-2-(7-Fluoro 6-methoxy- -2,3-dihydro-1H-3a-aza-cyclopenta[a]inden-8-yl)-1-methyl-ethylamine hydrochloride The product of example 16 was obtained from (S)-[2-(7-Fluoro-6-hydroxy-2,3-dihydro-1H-3a-aza-cyclopenta[a]inden-8-yl)-1-methyl-ethyl]-carbamic acid tert-butyl ester by reaction with methyliodide in dimethylformamide in the presence of sodium hydride and cleavage of the tert.butyloxycarbonyl protective group with hydrochloric acid in ethyl acetate.

Example 17

(S)-2-[7-Fluoro-6-(2-methoxy-ethoxy)-2,3-dihydro-1H-3a-aza-cyclopenta[a]inden-8-yl]-methyl-ethylamine hydrochloride By the same general procedure as in example 2 the title compound was obtained from (S)-[2-(7-Fluoro-6-hydroxy-2,3-dihydro-1H-3a-aza-cyclopenta[a]inden-8-yl)-1-methyl-ethyl]-carbamic acid tert-butyl ester.

Example 18

(S)-2-[7-Fluoro-6-(3-methoxy-propoxy)-2,3-dihydro-1H-3a-aza-cyclopenta[a]inden-8-yl]-1-methyl-ethylamine hydrochloride By the same general procedure as in example 5 the title compound was obtained from (S)-[2-(7-Fluoro-6-hydroxy-2,3-dihydro-1H-3a-aza-cyclopenta[a]inden-8-yl)-1-methyl-ethyl]-carbamic acid tert-butyl ester.

Example 19

(S)-2-[8-(2-Amino-propyl)-7-fluoro-2,3-dihydro-1H-3a-aza-cyclopenta[a]inden-6-yloxy]-ethanol hydrochloride By the same general procedure as in example 4 the title compound was obtained from (S)-[2-(7-fluoro-6-hydroxy-2,3-dihydro-1H-3a-aza-cyclopenta[a]inden-8-yl)-1-methyl-ethyl]-carbamic acid tert-butyl ester.

Example 20

(S)-2-(6-Cyclopropoxy-7-fluoro-2,3-dihydro-1H-3a-aza-cyclopenta[a]inden-8-yl)-1-methyl-ethylamine hydrochloride By the same general procedure as in example example 3 the title compound was obtained from 7-fluoro-2,3-dihydro-1H-3a-aza-cyclopenta[a]inden-6-ol.

Example A

Tablets containing the following ingredients can be manufactured in a conventional manner:

| Ingredients | Per tablet |
| --- | --- |
| Compound of formula I | 10.0–300.0 mg |
| Lactose | 125.0 mg |
| Maize starch | 75.0 mg |
| Talc | 4.0 mg |
| Magnesium stearate | 1.0 mg |

Example B

Capsules containing the following ingredients can be manufactured in a conventional manner:

| Ingredients | Per capsule |
| --- | --- |
| Compound of formula I | 100.0 mg |
| Lactose | 150.0 mg |
| Maize starch | 20.0 mg |
| Talc | 5.0 mg |

Example C

Injection solutions can have the following composition:

| Compound of formula I | 10.0 mg |
|---|---|
| Sodium chloride | q.s mg |
| Water for injection solutions | ad 2.0 ml |

What is claimed is:
1. A compound of formula

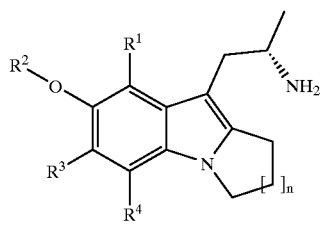

wherein
$R^1$ is hydrogen or fluoro;
$R^2$ is selected from the group consisting of methyl, ethyl, cyclopropyl, heteroarylalkyl, alkoxyalkyl, 3-oxetanyl, 3-tetrahydrofuranyl, 2-tetrahydrofuranylmethyl, 3-tetrahydrofuranyl methyl and hydroxyalkyl, wherein hydroxyalkyl or alkoxyalkyl are optionally independently substituted with at least one substituent selected from the group consisting of monofluoromethyl, difluoromethyl, trifluoromethyl, alkoxy and hydroxy;
$R^3$ is hydrogen or fluoro;
$R^4$ is hydrogen or methyl; and
n is 1, 2 or 3;
or a pharmaceutically acceptable salt, solvate or ester thereof provided that at least one of $R^1$ and $R^3$ is fluoro when $R^2$ is methyl.

2. A compound of formula I according to claim 1, wherein $R^2$ is selected from the unsubstituted group consisting of ethyl, cyclopropyl, aralkyl, heteroarylalkyl, alkoxyalkyl, 3-oxetanyl, 3-tetrahydrofuranyl, 2-tetrahydrofuranylmethyl, 3-tetrahydrofuranylmethyl and hydroxyalkyl, or said hydroxyalkyl and said alkoxyalkyl are each independently substituted with trifluoromethyl, alkoxy or hydroxy.

3. A compound according to claim 2, wherein $R^2$ is ethyl, methoxyethyl, cyclopropyl, hydroxyethyl, methoxypropyl, methoxybutyl, ethoxyethyl, ethoxypropyl, methoxyethoxyethyl, methoxyethoxypropyl or hydroxyethyl.

4. A compound of formula I according to claim 3, wherein $R^2$ is ethyl.

5. A compound of formula I according to claim 3, wherein $R^2$ is methoxypropyl.

6. A compound of formula I according to claim 1, wherein n is 1.

7. A compound of formula I according to claim 1, wherein $R^1$ is hydrogen.

8. A compound of formula I according to claim 1, wherein $R^1$ is fluoro.

9. A compound of formula I according to claim 1, wherein $R^1$ is hydrogen.

10. A compound of formula I according to claim 1, wherein $R^3$ is fluoro.

11. A compound of formula I according to claim 1, wherein $R^4$ is hydrogen.

12. A compound of formula I according to claim 1, wherein the compound is (S)-2-(6-ethoxy-2,3-dihydro-1H-3a-aza-cyclopenta[a]inden-8-yl)-1-methyl-ethylamine.

13. A compound of formula I according to claim 1, wherein the compound is (S)-2-[6-(2-methoxy-ethoxy)-2,3-dihydro-1H-3a-aza-cyclopenta[a]inden-8-yl]-1-methyl-ethylamine.

14. A compound of formula I according to claim 1, wherein the compound is (S)-2-(6-cyclopropoxy-2,3-dihydro-1H-3a-aza-cyclopenta[a]inden-8-yl)-1-methyl-ethylamine.

15. A compound of formula I according to claim 1, wherein the compound is (S)-2-[8-(2-amino-propyl)-2,3-dihydro-1H-3a-aza-cyclopenta[a]inden-6-yloxy]-ethanol.

16. A compound of formula I according to claim 1, wherein the compound is (S)-2-[6-(3-methoxy-propoxy)-2,3-dihydro-1H-3a-aza-cyclopenta[a]inden-8-yl]-1-methyl-ethylamine.

17. A compound of formula I according to claim 1 selected from the group consisting of (S)-2-[6-(4-methoxy-butoxy)-2,3-dihydro-1H-3a-aza-cyclopenta[a]inden-8-yl]-1-methyl-ethylamine;

(S)-2-[6-(2-ethoxy-ethoxy)-2,3-dihydro-1H-3a-aza-cyclopenta[a]inden-8-yl]-1-methyl-ethylamine;

(S)-2-[6-(3-ethoxy-propoxy)-2,3-dihydro-1H-3a-aza-cyclopenta[a]inden-8-yl]-1-methyl-ethylamine;

(S)-2-{6-[2-(2-methoxy-ethoxy)-ethoxy]-2,3-dihydro-1H-3a-aza-cyclopenta[a]inden-8-yl}-1-methyl-ethylamine;

(S)-2-{6-[3-(2-methoxy-ethoxy)-propoxy]-2,3-dihydro-1H-3a-aza-cyclopenta[a]inden-8-yl}-1-methyl-ethylamine;

(S)-2-(6-ethoxy-5-fluoro-2,3-dihydro-1H-3a-aza-cyclopenta[a]inden-8-yl)-1-methyl-ethylamine;

(S)-2-[5-floro-6-(2-methoxy-ethoxy)-2,3-dihydro-1H-3a-aza-cyclopenta[a]inden-8-yl]-1methyl-ethylamine;

(S)-2-[5-fluoro-6-(3-methoxy-propoxy)-2,3-dihydro-1H-3a-aza-cyclopenta[a]inden-8-yl]-1-methyl-ethylamine;

(S)-2-[8-(2-amino-propyl)-5-fluoro-2,3-dihydro-1H-3a-aza-cyclopenta[a]inden-6-yloxy]-ethanol;

(S)-2-(6-ethoxy-7-fluoro-2,3-dihydro-1H-3a-aza-cyclopenta[a]inden-8-yl)-1-methyl-ethylamine;

(S)-2-(7-fluoro-6-methoxy-2,3-dihydro-1H-3a-aza-cyclopenta[a]inden-8-yl)-1-methyl-ethylamine;

(S)-2-[7-fluoro-6-(2-methoxy-ethoxy)-2,3-dihydro-1H-3a-aza-cyclopenta[a]inden-8-yl]-methyl-ethylamine;

(S)-2-[7-fluoro-6-(3-methoxy-propoxy)-2,3-dihydro-1H-3a-aza-cyclopenta[a]inden-8-yl]-1-methyl-ethylamine;

(S)-2-[8-(2-amino-propyl)-7-fluoro-2,3-dihydro-1H-3a-aza-cyclopenta[a]inden-6-yloxy]-ethanol; and (S)-2-(6-cyclopropoxy-7-fluoro-2,3-dihydro-1H-3a-aza-cyclopenta[a]inden-8-yl)-1-methyl-ethylamine.

18. A process for the preparation of a compound of formula I according to claim 1 comprising deprotecting a compound of formula

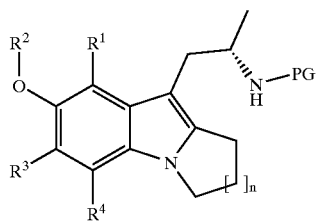

wherein R¹ to R⁴ and n are defined in the specification and PG represents a protecting group.

19. A pharmaceutical composition comprising a compound of formula I

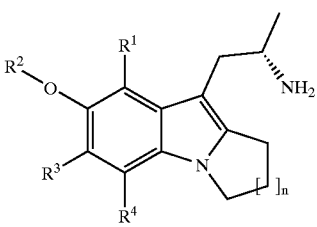

wherein
R¹ is hydrogen or fluoro;
R² is selected from the group consisting of methyl, ethyl, cyclopropyl, heteroarylalkyl, alkoxyalkyl, 3-oxetanyl, 3-tetrahydrofuranyl, 2-tetrahydrofuranylmethyl, 3-tetrahydrofuranylmethyl and hydroxyalkyl, wherein hydroxyalkyl or al alkoxyalkyl are optionally independently substituted with at least one substituent selected from the group consisting of monofluoromethyl, difluoromethyl, trifluoromethyl, alkoxy and hydroxy;
R³ is hydrogen or fluoro;
R⁴ is hydrogen or methyl; and
n is 1, 2 or 3;
or a pharmaceutically acceptable salt, solvate or ester thereof provided that at least one of R¹ and R³ is fluoro when R² is methyl, and a therapeutically inert carrier.

20. The pharmaceutical composition of claim 19 further comprising a lipase inhibitor.

21. The pharmaceutical composition of claim 20 wherein said lipase inhibitor is orlistat.

22. A pharmaceutical composition comprising a therapeutically effective amount of (S)-2-[6-(3-methoxy-propoxy)-2,3-dihydro-1H-3a-aza-cyclopenta[a]inden-8-yl]-1-methyl-ethylamine or a salt, solvate or ester thereof and a therapeutically inert carrier.

23. The pharmaceutical composition of claim 22 further comprising a therapeutically effective amount of a lipase inhibitor.

24. The pharmaceutical composition of claim 23 wherein the lipase inhibitor is orlistat.

25. A pharmaceutical composition comprising a therapeutically effective amount of (S)-2-(6-ethoxy-2,3-dihydro-1H-3a-aza-cyclopenta[a]inden-8-yl)-1-methyl-ethylamine or a salt, solvate or ester thereof and a therapeutically inert carrier.

26. The pharmaceutical composition of claim 25 further comprising a therapeutically effective amount of a lipase inhibitor.

27. The pharmaceutical composition of claim 26 wherein the lipase inhibitor is orlistat.

28. A method of modulating 5-HT₂ receptors in a mammal comprising administration of a therapeutically effective amount of a compound of formula I

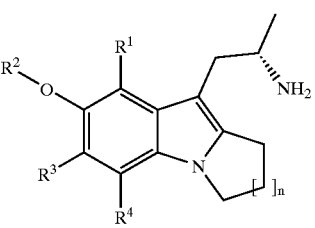

wherein
R¹ is hydrogen or fluoro;
R² is selected from the group consisting of methyl, ethyl, cyclopropyl, heteroarylalkyl, alkoxyalkyl, 3-oxetanyl, 3-tetrahydrofuranyl, 2-tetrahydrofuranylmethyl, 3-tetrahydrofuranylmethyl and hydroxyalkyl, wherein hydroxyalkyl or alkoxyalkyl are optionally independently substituted with at least one substituent selected from the group consisting of monofluoromethyl, difluoromethyl, trifluoromethyl, alkoxy and hydroxy;
R³ is hydrogen or fluoro;
R⁴ is hydrogen or methyl; and
n is 1, 2 or 3;
or a pharmaceutically acceptable salt, solvate or ester thereof, provided that at least one of R¹ and R³ is fluoro when R² is methyl, to a mammal in need of such modulation.

29. A method of treatment of eating disorders and obesity comprising administration of a therapeutically effective amount of a compound of formula I

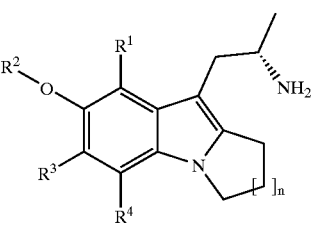

wherein
R¹ is hydrogen or fluoro;
R² is selected from the group consisting of methyl, ethyl, cyclopropyl, heteroarylalkyl, alkoxyalkyl, 3-oxetanyl, 3-tetrahydrofuranyl, 2-tetrahydrofuranylmethyl, 3-tetrahydrofuranylmethyl and hydroxyalkyl, wherein hydroxyalkyl or alkoxyalkyl are optionally independently substituted with at least one substituent selected from the group consisting of monofluoromethyl, difluoromethyl, trifluoromethyl, alkoxy and hydroxy;
R³ is hydrogen or fluoro;
R⁴ is hydrogen or methyl; and
n is 1, 2 or 3;
or a pharmaceutically acceptable salt, solvate or ester thereof, provided that at least one of R¹ and R³ is fluoro when R² is methyl, to a patient in need of such treatment.

30. The method of treatment of claim 29 further comprising administration of a therapeutically effective amount of a lipase inhibitor.

31. The method of treatment of claim 30 wherein said lipase inhibitor is orlistat.

32. A method of treatment of diabetes mellitus, Type I diabetes, Type II diabetes, diabetes secondary to pancreatic disease, diabetes related to steroid use, Type III diabetes, diabetes insipidus, hyperglycaemia, diabetic complications and insulin resistance comprising administration of a therapeutically effective amount of a compound of formula I

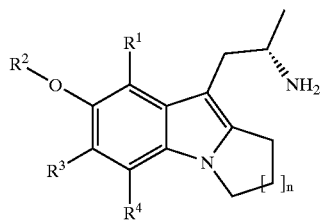

(I)

wherein $R^1$ is hydrogen or fluoro;

$R^2$ is selected from the group consisting of methyl, ethyl, cyclopropyl, heteroarylalkyl, alkoxyalkyl, 3-oxetanyl, 3-tetrahydrofuranyl, 2-tetrahydrofuranylmethyl, 3-tetrahydrofuranylmethyl and hydroxyalkyl, wherein hydroxyalkyl or alkoxyalkyl are optionally independently substituted with at least one substituent selected from the group consisting of monofluoromethyl, difluoromethyl, trifluoromethyl, alkoxy and hydroxy;

$R^3$ is hydrogen or fluoro;

$R^4$ is hydrogen or methyl; and n is 1, 2 or 3;

or a pharmaceutically acceptable salt, solvate or ester thereof, provided that at least one of $R^1$ and $R^3$ is fluoro when $R^2$ is methyl, to a patient in need of such treatment.

33. A method of treatment of type II diabetes comprising administration of a therapeutically effective amount of a compound of formula I

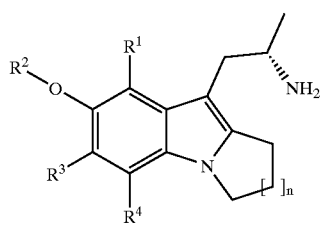

(I)

wherein $R^1$ is hydrogen or fluoro;

$R^2$ is selected from the group consisting of methyl, ethyl, cyclopropyl, heteroarylalkyl, alkoxyalkyl, 3-oxetanyl, 3-tetrahydrofuranyl, 2-tetrahydrofuranylmethyl, 3-tetrahydrofuranylmethyl and hydroxyalkyl, wherein hydroxyalkyl or alkoxyalkyl are optionally independently substituted with at least one substituent selected from the group consisting of monofluoromethyl, difluoromethyl, trifluoromethyl, alkoxy and hydroxy;

$R^3$ is hydrogen or fluoro; $R^4$ is hydrogen or methyl; and n is 1, 2 or 3;

or a pharmaceutically acceptable salt, solvate or ester thereof provided that at least one of $R^1$ and $R^3$ is fluoro when $R^2$ is methyl, to a patient in need of such treatment.

34. The method of treatment of claim 33 further comprising administration of a therapeutically effective amount of a lipase inhibitor.

35. The method of treatment of claim 34 wherein said lipase inhibitor is orlistat.

36. A method of treatment of obesity comprising administering a therapeutically effective amount of (S)-2-(6-ethoxy-2,3-dihydro-1H-3a-aza-cyclopenta[a]inden-8-yl)-1-methyl-ethylamine or a salt, solvate or ester thereof to a patient in need of such treatment.

37. The method of treatment of claim 36 further comprising administering a therapeutically effective amount of a lipase inhibitor.

38. The method of treatment of claim 37 wherein said lipase inhibitor is orlistat.

39. A method of treatment of type II diabetes comprising administering a therapeutically effective amount of (S)-2-(6-ethoxy-2,3-dihydro-1H-3a-aza-cyclopenta[a]inden-8-yl)-1-methyl-ethylamine or a salt, solvate or ester thereof to a patient in need of such treatment.

40. The method of treatment of claim 39 further comprising administering a therapeutically effective amount of a lipase inhibitor.

41. The method of treatment of claim 40 wherein said lipase inhibitor is orlistat.

42. A method of treatment of type II diabetes comprising administering a therapeutically effective amount of (S)-2-[6-(3-methoxy-propoxy)-2,3-dihydro-1H-3a-aza-cyclopenta[a]inden-8-yl]-1-methyl-ethylamine or a salt, solvate or ester thereof to a patient in need of such treatment.

43. The method of treatment of claim 42 further comprising administering a therapeutically effective amount of a lipase inhibitor.

44. The method of treatment of claim 43 wherein said lipase inhibitor is orlistat.

45. A method of treatment of obesity comprising administering a therapeutically effective amount of (S)-2-[6-(3-methoxy-propoxy)-2,3-dihydro-1H-3a-aza-cyclopenta[a]inden-8-yl]-1-methyl-ethylamine or a salt, solvate or ester thereof to a patient in need of such treatment.

46. The method of treatment of claim 45 further comprising administering a therapeutically effective amount of a lipase inhibitor.

47. The method of treatment of claim 46 wherein said lipase inhibitor is orlistat.

* * * * *

UNITED STATES PATENT AND TRADEMARK OFFICE
CERTIFICATE OF CORRECTION

PATENT NO. : 6,610,685 B2
DATED : August 26, 2003
INVENTOR(S) : Jonathan Mark Bentley et al.

Page 1 of 1

It is certified that error appears in the above-identified patent and that said Letters Patent is hereby corrected as shown below:

Title page,
Item [75], Inventors, delete "Jonathan Mark Bentley, Wokingham (GB);
Michael John Bickerdike, Wokingham (GB); Paul Hebeisen, Basie (CH);
Guy Anthony Kennett, Wokingham (GB); Sean Lightowler, Wokingham (GB);
Patrizio Mattei, Riechen (CH); Jacques Mizrahi, Basle (CH);
Timothy James Morley, Wokingham (GB); Jean-Marc Plancher, Knoeringue (FR);
Hans Richter, Grenzach-Wyhlen (DE); Stephan Roever, Inzlingen (DE);
Sven Taylor, Riedisheim (FR); Steven Paul Vickers Wokingham (GB)"

and insert -- Jonathan Mark Bentley, Wokingham (GB);
Michael John Bickerdike, Wokingham (GB); Paul Hebeisen, Basle (CH);
Guy Anthony Kennett, Wokingham (GB); Sean Lightowler, Wokingham (GB);
Patrizio Mattei, Riechen (CH); Jacques Mizrahi, Basle (CH);
Timothy James Morley, Wokingham (GB); Jean-Marc Plancher, Knoeringue (FR);
Hans Richter, Grenzach-Wyhlen (DE); Stephan Roever, Inzlingen (DE);
Sven Taylor, Riedisheim (FR); Steven Paul Vickers Wokingham (GB) --.

Column 37,
Line 29, delete "3-tetrahydrofuranyl methyl and hydroxyalkyl, wherein" and insert
-- 3-tetrahydrofuranylmethyl and hydroxyalkyl, wherein --.

Column 39,
Line 42, delete "thereof provided that at least one of $R^1$ and $R^3$ is fluoro" and insert
-- thereof, provided that at least one of R1 and R3 is fluoro --.

Signed and Sealed this

Tenth Day of February, 2004

JON W. DUDAS
*Acting Director of the United States Patent and Trademark Office*